US011141324B2

(12) United States Patent
Moritani

(10) Patent No.: US 11,141,324 B2
(45) Date of Patent: Oct. 12, 2021

(54) METHOD FOR MANUFACTURING ABSORBENT ARTICLE AND ABSORBENT SANITARY ARTICLE

(71) Applicant: DAIO PAPER CORPORATION, Ehime (JP)

(72) Inventor: Akie Moritani, Ehime (JP)

(73) Assignee: DAIO PAPER CORPORATION, Ehime (JP)

(*) Notice: Subject to any disclaimer, the term of this patent is extended or adjusted under 35 U.S.C. 154(b) by 1020 days.

(21) Appl. No.: 15/528,314

(22) PCT Filed: Nov. 10, 2015

(86) PCT No.: PCT/JP2015/081626
§ 371 (c)(1),
(2) Date: May 19, 2017

(87) PCT Pub. No.: WO2016/080247
PCT Pub. Date: May 26, 2016

(65) Prior Publication Data
US 2017/0312144 A1 Nov. 2, 2017

(30) Foreign Application Priority Data

Nov. 19, 2014 (JP) .............................. JP2014-234857

(51) Int. Cl.
*A61F 13/511* (2006.01)
*A61F 13/15* (2006.01)
(Continued)

(52) U.S. Cl.
CPC ........ *A61F 13/51104* (2013.01); *A61F 13/15* (2013.01); *A61F 13/15699* (2013.01);
(Continued)

(58) Field of Classification Search
CPC ............ A61F 13/51104; A61F 13/5116; A61F 13/51476; A61F 13/511; A61F 13/49011;
(Continued)

(56) References Cited

U.S. PATENT DOCUMENTS 10,470,945 B2* 11/2019 Moritani ........... A61F 13/15707
2003/0181882 A1* 9/2003 Toyoshima ......... A61F 13/5123
604/367

(Continued)

FOREIGN PATENT DOCUMENTS

JP 2005314842 A 11/2005
JP 2008148807 A 7/2008
(Continued)

*Primary Examiner* — Michele M Kidwell
(74) *Attorney, Agent, or Firm* — Muncy, Geissler, Olds and Lowe, P.C.

(57) ABSTRACT

Provided is an absorbent article which includes a top sheet having extruded protrusions and a second sheet bonded to the top sheet and has adequate softness, satisfactory appearance, and yet prevents wrinkles in the top sheet along the MD. The problem is solved by a method of producing an absorbent article including forming the extruded protrusions through embossing of non-woven fabric to be a top sheet transferred by being drawn from downstream of a production line; and then bonding the non-woven fabric and a material of a second sheet in a bonding pattern formed by aligning the material of the second sheet 40 with the back face of the non-woven fabric having extruded protrusions, forming rows of plurality of top-second bonded portions at intervals in the CD in regions between the extruded protrusions adjacent each other in the MD so as to be provided across the center positions of the regions in the CD, and compressing the non-woven fabric in areas between the top-second bonded portions in the rows in the CD without welding of the non-woven fabric and the material of the second sheet.

17 Claims, 18 Drawing Sheets

(51) Int. Cl.

| | | |
|---|---|---|
| *A61F 13/49* | (2006.01) | |
| *A61F 13/512* | (2006.01) | |
| *A61F 13/494* | (2006.01) | |
| *A61F 13/514* | (2006.01) | |
| *A61F 13/515* | (2006.01) | |
| *B32B 3/30* | (2006.01) | |
| *B32B 5/02* | (2006.01) | |
| *B32B 7/12* | (2006.01) | |
| *B32B 27/32* | (2006.01) | |
| *B32B 37/12* | (2006.01) | |
| *B32B 38/06* | (2006.01) | |

(52) U.S. Cl.
CPC .. *A61F 13/15731* (2013.01); *A61F 13/15739* (2013.01); *A61F 13/49* (2013.01); *A61F 13/49406* (2013.01); *A61F 13/511* (2013.01); *A61F 13/515* (2013.01); *A61F 13/5116* (2013.01); *A61F 13/5125* (2013.01); *A61F 13/51476* (2013.01); *B32B 3/30* (2013.01); *B32B 5/022* (2013.01); *B32B 7/12* (2013.01); *B32B 27/32* (2013.01); *B32B 37/1207* (2013.01); *B32B 38/06* (2013.01); *A61F 2013/4948* (2013.01); *B32B 2037/1215* (2013.01); *B32B 2307/726* (2013.01); *B32B 2555/02* (2013.01)

(58) Field of Classification Search
CPC .......... A61F 13/53743; A61F 13/51394; A61F 13/5633; A61F 13/15; A61F 13/15699; A61F 13/15731; A61F 13/5125; A61F 2013/515; B32B 2555/02; B32B 3/30; B32B 38/06
See application file for complete search history.

(56) References Cited

U.S. PATENT DOCUMENTS

| | | | |
|---|---|---|---|
| 2010/0249740 A1* | 9/2010 | Miyamoto | ........ A61F 13/51104 604/384 |
| 2012/0059343 A1* | 3/2012 | Kume | ..................... B29C 65/02 604/379 |
| 2013/0280481 A1* | 10/2013 | Mitsuno | ................... D04H 5/06 428/131 |
| 2014/0163507 A1 | 6/2014 | Kudo et al. | |
| 2015/0119843 A1* | 4/2015 | Kurihara | ............. A61F 13/5116 604/385.101 |
| 2015/0238370 A1* | 8/2015 | Uda | ..................... A61F 13/534 604/370 |
| 2015/0290050 A1 | 10/2015 | Wada | |

FOREIGN PATENT DOCUMENTS

| | | |
|---|---|---|
| JP | 2009172354 | 8/2009 |
| JP | 2010150686 A | 7/2010 |
| JP | 2011234896 A | 11/2011 |
| JP | 2012-239712 A | 12/2012 |
| JP | 2014188129 A | 10/2014 |
| WO | WO-2009028236 A1 | 3/2009 |
| WO | WO2014050310 A1 | 4/2014 |

* cited by examiner

METHOD FOR MANUFACTURING ABSORBENT ARTICLE AND ABSORBENT SANITARY ARTICLE

TECHNICAL FIELD

The present invention relates to absorbent articles, such as disposable diapers and sanitary napkins.

BACKGROUND ART

Such absorbent articles each include an absorber and a liquid-pervious top sheet that covers the front side of the absorber. Excretion, such as urine or blood, passes through the top sheet and is absorbed and retained in the absorber. Examples of traditional top sheets for absorbent articles include those composed of non-woven fabric produced through various processes, the non-woven fabric having holes formed through secondary processing, and perforated film composed of synthetic resin, such as polyethylene. Many absorbent articles include a second sheet composed of bulky non-woven fabric bonded to the back face of the top sheet to prevent reflowing of the excretion from the top sheet to the skin of the wearer.

Absorbent articles should not only prevent leakage of excretion, such as urine, but also prevent discomfort and irritation of the skin due to contact of the excretion, such urine, to the skin. In recent years, an absorbent article having a top sheet composed of non-woven fabric have been produced through embossing of the top sheet to produce a large number of domical extruded protrusions that can reduce the contact surface of the top sheet to the skin of the wearer and soften the top sheet in the contact area with the skin, as disclosed in Patent Documents 1 to 3. In particular, the absorbent article disclosed in Patent Document 3 includes a top sheet and a second sheet bonded to the areas surrounding the extruded protrusions in the top sheet (the bottom areas of the depressions provided between the protrusions). This configuration is highly suitable for firm extruded protrusions that can be maintained even under pressure in a package until the absorbent article is used after distribution, resulting in satisfactory absorbency and pleasing appearance. The embossed top sheet is highly functional, appears functionally beautiful to users, and thus is a very important factor for pleasing appearance.

Such a top sheet and second sheet can be bonded with triple roll processing equipment, such as that illustrated in FIG. 12. In detail, the processing equipment for top sheets includes a squeeze roll 90 having a large number of squeeze convexes 90a on the circumferential surface thereof; a recessed roll 91 facing the squeeze roll 90 and having bonding convexes 91b provided between adjacent concaves 91a that correspond to the squeeze convexes 90a; and a bonding roll 92 that faces the recessed roll 91. The material 30S for the top sheet is fed under a certain level of stretching tension applied from downstream of the production line and passes between the squeeze roll 90 and the recessed roll 91 where the convexes of the squeeze roll 90 are pushed into the concaves 91a of the recessed roll 91 to form a large number of extruded protrusions or projections 31. Then, while the material 30S of the top sheet is wound around the recessed roll 91 so as to be guided by the rotation of the recessed roll 91, another material 40S for the second sheet is also fed under a certain level of stretching tension applied samely from the downstream of the production line. The material 30S for the top sheet and the material 40S for the second sheet are fed between the recessed roll 91 and the bonding roll 92 and are bonded by thermocompression between the bonding convexes 91b of the recessed roll 91 and the outer circumferential surface of the bonding roll 92, to form top-second bonded portions 80.

Unfortunately, the top sheet according to Patent Document 3 has many wrinkles along the machine direction (MD) (conveying direction of the sheet) of the top sheet processing equipment at a predetermined pitch in the cross direction (CD) (orthogonal to the MD), impairing the pleasing appearance, as in the comparative sample illustrated in FIG. 14.

CITATION LIST

Patent Document

Patent Document 1: Japanese Unexamined Patent Application Publication No. 2005-314842
Patent Document 2: Japanese Unexamined Patent Application Publication No. 2010-150686
Patent Document 3: Japanese Unexamined Patent Application Publication No. 2011-234896

SUMMARY OF INVENTION

Technical Problem

An object of the present invention is to provide an absorbent article that includes a top sheet having extruded protrusions and a second sheet bonded to the top sheet and has adequate softness, satisfactory appearance and does not have wrinkles along the MD in the top sheet.

Solution to Problem

The present inventor has conducted intensive studies on the wrinkles and discovered that the wrinkles in the top sheet extend through the center in the CD of the protrusions aligned in the MD. Thus, the inventor came to the conclusion that dot-shaped top-second bonded portions provided between the extruded protrusions aligned in the MD at center positions in the CD corresponding to the center portions in the CD of the extruded protrusions along the CD are not sufficient for prevention of wrinkles in the top sheet, contrary to what was first expected for prevention of remained wrinkles. In a study conducted to determine the cause of this, it was discovered that the effect of wrinkle prevention is enhanced through an increase in the CD length of the top-second bonded portions. Such wrinkle prevention causes an increase in the size of the top-second bonded portions, which could impair softness and appearance. The present invention described below is based on such finding.

<The Invention of Claim 1>

A method of producing an absorbent article comprising an absorber, a liquid pervious top sheet comprising non-woven fabric covering the front side of the absorber, and a second sheet bonded to the back face of the top sheet, wherein, a large number of extruded protrusions embossed from the back side to the front side of the top sheet is arrayed at intervals in the width direction and the front-back direction respectively, and a large number of top-second bonded portions arrayed in an intermittent bonding pattern in the width direction and the front-back direction is provided through pressure welding of the top sheet and the second sheet at areas between the extruded protrusions aligned in the width direction and the front-back direction, the method comprising:

assembling of the top sheet and the second sheet, the assembling comprising:
  transferring the non-woven fabric to be the top sheet by being drawn from downstream of a production line while forming the extruded protrusions in the non-woven fabric through embossing;
  after that, aligning a material of the second sheet with the back face of the non-woven fabric having the extruded protrusions; and
  bonding the non-woven fabric and the material of the second sheet into a bonding pattern such that in regions between the extruded protrusions adjacent each other in the MD, rows of a plurality of top-second bonded portions disposed at intervals in the CD are provided through the center positions of the regions in the CD, while in areas between the top-second bonded portions in the CD, the non-woven fabric is compressed without welding of the non-woven fabric and the material of the second sheet.

(Advantageous Effects)

By bonding the non-woven fabric to be the top sheet and the material of the second sheet in the bonding pattern, the pressure-welded portions (top-second bonded portions) and the unwelded compressed portions are formed during the bonding of the non-woven fabric to be the top sheet and the material of the second sheet such that they alternate in the CD and they are provided across vertical wrinkles that may form during formation of the extruded protrusions aligned in the MD in the non-woven fabric to be the top sheet. Thus, the top-second bonded portions can be formed while the vertical wrinkles are significantly stretch, and this stretched state can be maintained or substantially maintained even after production. The bonded areas (top-second bonded portions) intermittently aligned in the CD establish adequate softness and satisfactory appearance.

<The Invention of Claim 2>

The method of producing an absorbent article according to claim 1, wherein in the bonding pattern, the top-second bonded portions are absent, the non-woven fabric and the material of the second sheet are unwelded, and the non-woven fabric is compressed in the center positions in the CD corresponding to center portions in the CD of the extruded protrusions adjacent each other in the MD.

(Advantageous Effects)

The absence of the top-second bonded portions in the center positions in the CD contributes to the roundness of the extruded protrusions while promotes the formation of vertical wrinkles at the center positions in the CD. The invention according to claim 2 provides a compressed portion at the center positions in the CD, which contributes to the roundness of the extruded protrusions while sufficiently preventing vertical wrinkles.

<The Invention of Claim 3>

The method of producing an absorbent article according to claim 1, wherein, in the bonding pattern,
  a plurality of rows of the top-second bonded portions is formed at intervals in the MD in the regions, each row comprising the plurality of top-second bonded portions aligned in the CD at intervals,
  the non-woven fabric and the material of the second sheet are unwelded and the non-woven fabric is compressed in areas between the top-second bonded portions in the CD, and
  the non-woven fabric and the material of the second sheet are unwelded and the non-woven fabric is more lightly compressed in areas between the top-second bonded portions in the MD compared to the areas in the CD.

(Advantageous Effects)

Such a bonding pattern increases the areas between the extruded protrusions in the MD, and the areas between the top-second bonded portions in the MD are more lightly compressed compared to the areas in the CD (or not compressed at all). This can enhance softness and appearance.

<The Invention of Claim 4>

The method of producing an absorbent article according to one of claims 1 to 3, wherein,
  with a squeeze roll having a large number of squeeze convexes disposed in a pattern corresponding to the pattern of the extruded protrusions on the circumferential surface of the squeeze roll, a recessed roll facing the squeeze roll, having concaves corresponding to the squeeze convexes, and having bonding convexes that form the top-second bonded portions and compression convexes provided between the concaves, and a bonding roll facing the recessed roll,
  the non-woven fabric to be the top sheet is transferred by being drawn from downstream of the production line and is fed between the squeeze roll and the recessed roll, the squeeze convexes of the squeeze roll are pushed into the bonding concaves of the recessed roll to form the extruded protrusions and then, while the non-woven fabric to be the top sheet is wound around the rotating recessed roll so as to be guided directly, the material of the second sheet is being fed onto the outer side of the non-woven fabric to be the top sheet by being drawn from the downstream of the production line, the non-woven fabric to be the top sheet and the material of the second sheet are being fed between the recessed roll and the bonding roll, the non-woven fabric to be the top sheet and the material of the second sheet are pressure welded between the bonding convexes of the recessed roll and the outer circumferential surface of the bonding roll, to form the top-second bonded portions.

(Advantageous Effects)

A processing scheme for bonding the top sheet to the second sheet immediately after the extruded protrusions are formed and before the wrinkles can be absorbed causes ready formation of wrinkles. Thus, the method of producing an absorbent article according to the present invention is preferably applied to such a processing scheme.

<The Invention of Claim 5>

An absorbent article comprising:
  an absorber;
  a liquid pervious top sheet comprising a non-woven fabric covering the front side of the absorber; and
  a second sheet bonded to the back surface of the top sheet, wherein,
  a large number of extruded protrusions embossed from the back side to the front side of the top sheet is arrayed in the width direction and the front-back direction at intervals,
  a large number of dot-shaped top-second bonded portions disposed in an intermittent bonding pattern in the width direction and the front-back direction of the top sheet is provided through pressure welding of the top sheet at areas between the extruded protrusions adjacent each other in the width direction and the front-back direction and the second sheet, and
  rows of a plurality of top-second bonded portions are disposed in the top sheet at intervals in the CD in regions between the extruded protrusions adjacent each other in the MD so as to be provided across the center positions of the regions in the CD, and the areas between the top-second bonded portions in the CD comprise compressed portions in each of which the top sheet and the second sheet are unwelded and the top sheet is more highly compressed than the areas at both sides of the compressed portions in the MD.

(Advantageous Effects)

According to the present invention, the top-second bonded portions aligned at intervals in the CD can prevent a reduction in softness, while the compressed portions disposed in the areas aligned in the CD can prevent deformation of the extruded protrusions even under various forces applied during use and formation of vertical wrinkles. This reduces friction between the top sheet and the skin of the wearer due to a reduction in the contact area without impairing the softness of the portions in contact with the skin of the wearer.

By bonding the non-woven fabric to be the top sheet and the material of the second sheet in the bonding pattern consisting of the top-second bonded portions and the compressed portions in accordance with the method for producing an absorbent article described above, the pressure-welded portions (top-second bonded portions) and the unwelded compressed portions are disposed during the bonding of the non-woven fabric to be the top sheet and the material of the second sheet such that they alternate in the CD and they are provided across vertical wrinkles that may form during formation of the extruded protrusions aligned in the MD in the non-woven fabric to be the top sheet. Thus, the top-second bonded portions can be formed while the vertical wrinkles are significantly stretch, and this stretched state can be maintained even after production. The bonded portions (top-second bonded portions) intermittently aligned in the CD establish adequate softness and satisfactory appearance.

The "MD" and "CD" of an absorbent article respectively refer to the "MD" and "CD" of the processing equipment of the extruded protrusions, one corresponding to the front-back direction of the product while the other corresponding to the width direction of the product. The MD of the product corresponds to the direction of the orientation of the fiber in the non-woven fabric of the top sheet. The orientation of fiber is the extending direction of the fibers in the non-woven fabric. The orientation of fiber can be determined through a testing method in accordance with TAPPI Standard Method T481 for testing fiber orientation with zero-span tensile strength or a simple scheme for determining fiber orientation by the ratio of tensile strengths in the front-back direction to the with direction.

<The Invention of Claim 6>

The absorbent article according to claim 5, wherein the compressed portions are disposed and the top-second bonded portions are absent at the center positions in the CD corresponding to center portions in the CD of the extruded protrusions adjacent each other in the MD.

(Advantageous Effects)

The absence of the top-second bonded portions in the center positions in the CD contributes to the roundness of the extruded protrusions while promotes the formation of vertical wrinkles in the centers in the CD. The invention of claim 6 provides compressed portions in the center positions in the CD, which contributes to the roundness of the extruded protrusions while sufficiently preventing vertical wrinkles.

<The Invention of Claim 7>

The absorbent article according to claim 5 or 6, wherein, a plurality of rows of the top-second bonded portions is formed at intervals in the MD in the regions, each row comprising the plurality of top-second bonded portions aligned in the CD at intervals, the top sheet and the second sheet are unwelded and the top sheet is compressed in areas between the top-second bonded portions in the CD, and the top sheet and the second sheet are unwelded and the top sheet is more lightly compressed in areas between the top-second bonded portions in the MD compared to the areas between top-second bonded portions in the CD.

(Advantageous Effects)

Such a bonding pattern increases the areas between the extruded protrusions in the MD, and the areas between the top-second bonded portions in the MD is more lightly compressed compared to the areas in the CD (or not compressed at all). This can enhance softness and appearance.

<The Invention of Claim 8>

The absorbent article according to one of claims 5 to 7, wherein, the top-second bonded portions in the regions comprise dot-shaped bonded portions having an MD length 0.1 to 0.4 times the MD center pitch of the CD rows of the extruded protrusions adjacent each other in the MD and a CD length 0.1 to 0.4 times the CD center pitch of the MD rows of extruded protrusions adjacent each other in the CD, and the distance between adjacent top-second bonded portions in the CD among the rows of the plurality of top-second bonded portions disposed at intervals in the CD is 1 to 5 times the CD length of the top-second bonded portions.

(Advantageous Effects)

There is no particular limitation on the dimension or center pitch of the dot-shaped bonded portion but they are preferably within the range defined in claim 8.

<The Invention of Claim 9>

The absorbent article according to one of claims 5 to 8, wherein, the MD is the front-back direction of the absorbent article, and the CD is the width direction of the absorbent article, or the MD is the width direction of the absorbent article, and the CD is the front-back direction of the absorbent article.

(Advantageous Effects)

The same advantageous effect as those according to claim 5 are achieved.

Advantageous Effects of Invention

As described above, the present invention can provide an absorbent article that includes a top sheet having extruded protrusions and a second sheet bonded to the top sheet and has adequate softness, satisfactory appearance and does not have wrinkles along the MD of the top sheet.

DESCRIPTION OF EMBODIMENTS

Figure 1:
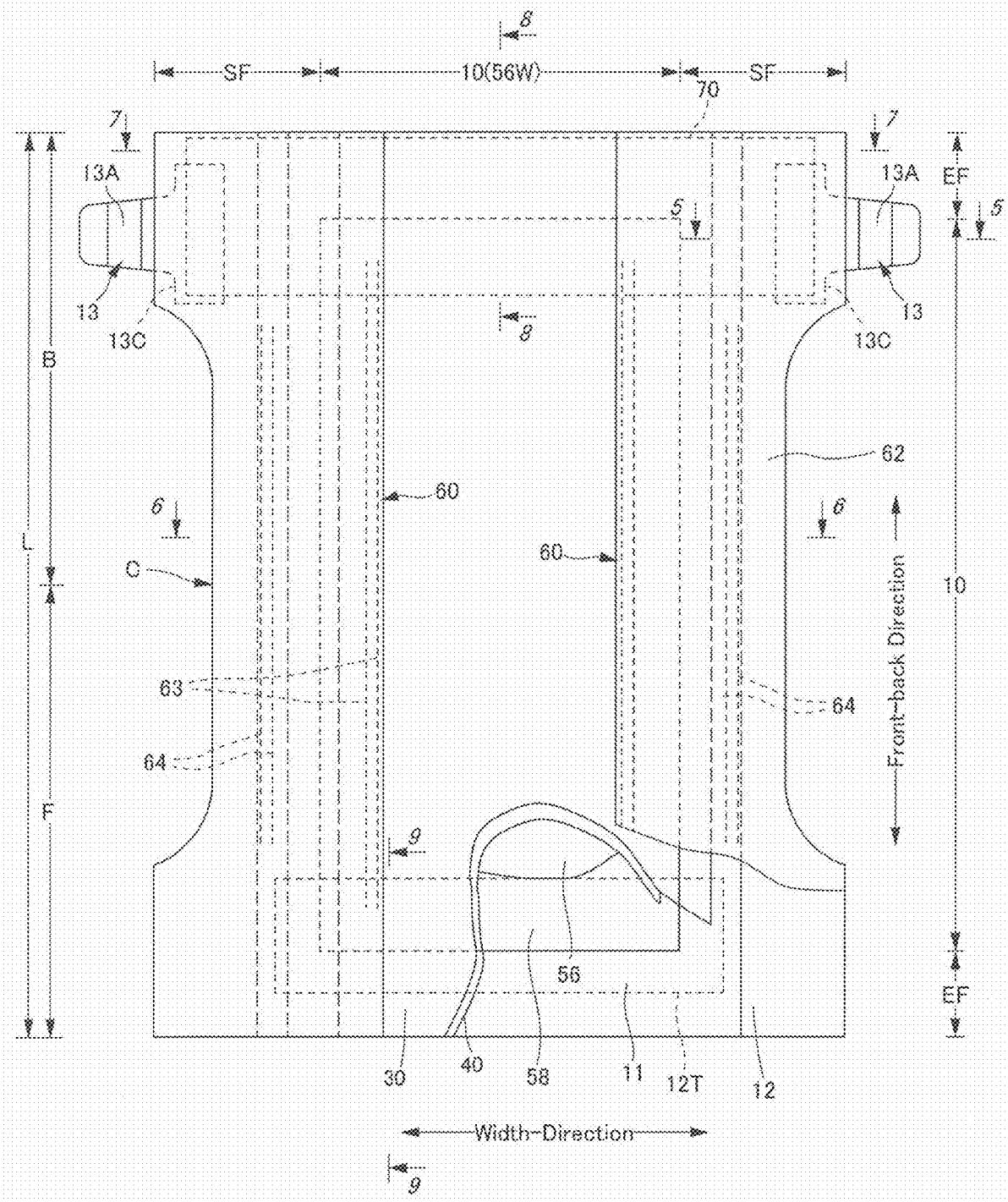
FIG. 1 is a plan view of the internal surface of an unfolded tape-type disposable diaper.

Embodiments of the present invention will now be described with reference to the accompanying drawings.

FIGS. 1 to 6 illustrate an example of tape-type disposable diaper. In the drawings, reference sign X indicates the entire width of the diaper exclusive of the fastening tapes and reference sign L indicates the entire length of the diaper. Fixing and bonding of the components other than those described below may be carried out in the same manner as those for known diapers. Any means for fixing and bonding may be appropriately selected, such as hotmelt adhesives and welding (thermowelding or ultrasonic welding).

Such a tape-type disposable diaper includes a liquid pervious top sheet that faces the body of the wearer and covers an area extending from the lower abdomen to the gluteal region over the crotch portion along the width direction; a main absorbent unit section 10 in which an absorbent element 50 is disposed between this section and a liquid impervious sheet disposed on the external surface side; and a ventral-side end flap section EF and a dorsal-side end flap section EF that do not include the absorbent element 50 and extend respectively from front and back ends of the main absorbent unit section 10.

The tape-type disposable diaper has a pair of side flap sections SF and SF extending at the lateral sides beyond the side edges of the main absorbent unit section 10. Fastening tapes 13 are provided on the dorsal sides of the side flap sections SF and SF.

In detail, the entire external surface of the main absorbent unit section 10 and the side flap sections SF and SF are composed of an outer sheet 12. In particular, in the main absorbent unit section 10, a liquid impervious sheet 11 is fixed to the internal surface side of the outer sheet 12 with an adhesive, such as a hotmelt adhesive. The absorbent element 50, a second sheet 40, and a top sheet 30 are layered on the internal surface side of the liquid impervious sheet 11 in this order. The top sheet 30 and the liquid impervious sheet 11 illustrated in the drawings have rectangular shapes, and lengths along the front-back direction and the width direction are slightly larger than those of the absorbent element 50. The peripheral portions of the top sheet 30 that extend off the edges of the absorbent element 50 are fixed to the peripheral portions of the liquid impervious sheet 11 that extend off the edges of the absorbent element 50 with a hotmelt adhesive. The liquid impervious sheet 11 is composed of a moisture permeable polyethylene film and has a width slightly larger than that of the top sheet 30.

Three-dimensional side gathers 60 and 60 protruding (erecting) toward the skin of the wearer are provided on the both sides of the main absorbent unit section 10. The three-dimensional side gathers 60 and 60 include gather sheets 62 and 62 that are fixed within an area extending from the above of the both sides of the top sheet 30 to the internal surfaces of the side flap sections SF and SF.

The materials and features of the individual components will now be described in order.

(Outer Sheet)

The outer sheet 12 supports the absorbent element 50 and fixes the disposable diaper to the wearer. The outer sheet 12 has a shape of an hourglass that is narrowed at a middle portion in the front-back direction on the both sides to surround the legs of the wearer.

A suitable example of the material of the outer sheet 12 is non-woven fabric but is not limited to this. There is no particular limitation on the kind of the non-woven fabric. Examples include synthetic fibers based on olefin, such as polyethylene and polypropylene, polyester, and polyamide; reproduced fibers, such as rayon and cupra; and natural fibers, such as cotton. The non-woven fabric may be produced through spunlacing, spunbonding, thermal bonding, air through bonding, needle punching or the like. Long-fibered non-woven fabrics, such as spunbonded non-woven fabrics, SMS non-woven fabrics, and SMMS non-woven fabrics, are suitable because of compatibility of texture and strength. The non-woven fabrics may be used in the form of a single layer or a plurality of layers. It is preferred that plurality of layers of non-woven fabric be bonded with a hotmelt adhesive. The fiber basis weight of the non-woven fabric is within the range of 10 to 50 g/m$^2$, preferably 15 to 30 g/m$^2$.

(Liquid Impervious Sheet)

There is no particular limitation on the material for the liquid impervious sheet 11. Examples include olefin resins such as polyethylene and polypropylene; laminated non-woven fabrics such as non-woven fabric layers disposed on polyethylene sheets; and non-woven fabrics provided with waterproof films that make the non-woven fabric substantially liquid impervious (the liquid impervious sheets include waterproof films and non-woven fabrics). Other examples include materials having liquid imperviousness and moisture permeability, which are suitable for avoiding stuffiness. An example sheet composed of a material having liquid imperviousness and moisture permeability is a microporous sheet produced through kneading an olefin resin, such as polyethylene resin or polypropylene resin, and an inorganic filler, forming a sheet with the kneaded materials, and monoaxially or biaxially stretching the sheet. Alternatively, the liquid impervious sheet 11 with liquid imperviousness without a water-proof film may be produced with a non-woven fabric composed of microdenier fiber or by enhancement of leak-proof properties through reduction of voids in the fiber under heat or pressure or application of a superabsorbent polymer, hydrophobic resin, or water-repellent agent.

(Top Sheet)

The top sheet 30 is composed of porous or non-porous non-woven fabric having liquid perviousness. There is no particular limitation on the kind of raw fiber for the non-woven fabric. Examples of such raw fiber include synthetic fibers based on olefin, such as polyethylene and polypropylene, polyester, and polyamide; reproduced fibers, such as rayon and cupra; natural fibers, such as cotton; and mixed fibers and composite fibers composed of two or more of these fibers. The non-woven fabric may be produced through any process. Examples of known processes include spun-lacing, spunbonding, thermal bonding, melt blowing, needle punching, air through bonding, and point bonding. For example, spunlacing is suitable for achieving softness and draping, whereas thermal bonding is suitable for bulkiness and softness.

The top sheet 30 may be composed of a single sheet or a layered sheet formed by sticking two or more sheets to each other. The top sheet 30 may be composed of a single sheet or two or more sheets in a planar direction.

(Second Sheet)

The second sheet 40 is bonded to the back face of the top sheet 30 to facilitate rapid migration of liquid excrement having passed through the top sheet 30 to the absorber 56 and prevent reflowing of the excretion through the top sheet 30. In the case where the second sheet 40 and the top sheet 30 are to be bonded through heat embossing or ultrasonic welding, it is preferred that the material of the second sheet 40 has approximately the same melting point as that of the top sheet 30. The second sheet 40 may be composed of non-woven fabric or a resin film having many permeable pores. The second sheet 40 may be composed of the same non-woven fabric as the top sheet 30 stated above. Non-woven fabric for the second sheet 40 is preferably higher in hydrophilicity and a fiber density than the non-woven fabric for the top sheet 30 for enhancement of migration of liquid from the top sheet 30 to the second sheet 40.

The second sheet 40 illustrated in the drawing has a width smaller than that of the absorbent element 50 and is disposed in the central area in the width direction of the absorbent element 50. Alternatively, the width of the second sheet 40 may be the same as that of the absorbent element 50. The length of the second sheet 40 in the front-back direction may be equal to the entire length of the diaper, equal to the entire length of the absorbent element 50, or a small length that mainly covers the area that receives the liquid.

(Three-Dimensional Side Gather)

Preferably, the three-dimensional side gathers 60 and 60 protruding (erect) from the using surface are provided on the both sides of the diaper to shut off urine or loose stool due to lateral migration along the top sheet 30 for preventing lateral leakage.

Figure 3:
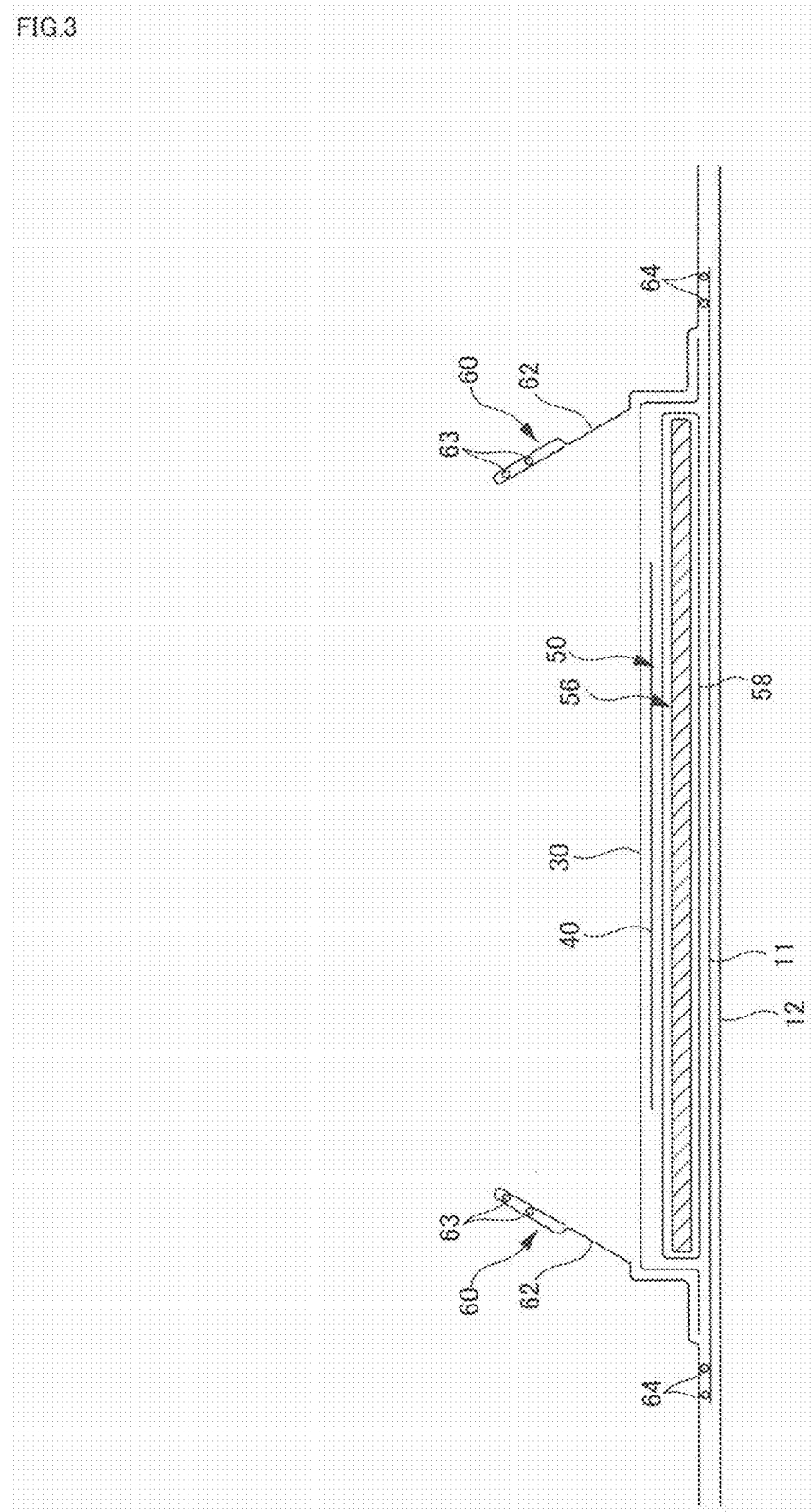
FIG. 3 is a cross-sectional view taken along line 6-6 in FIG. 1.
Figure 4:
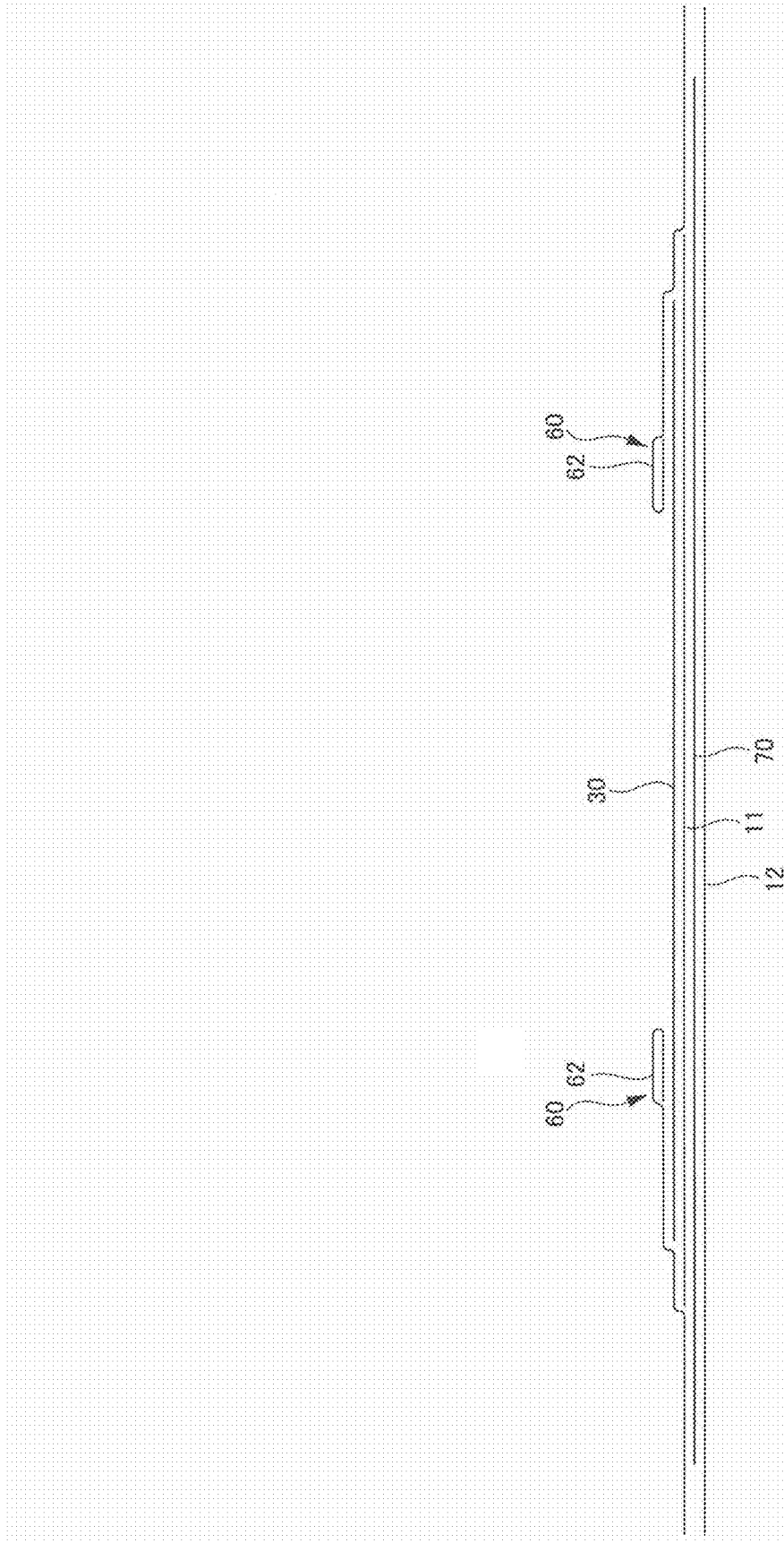
FIG. 4 is a cross-sectional view taken along line 7-7 in FIG. 1.

The three-dimensional side gathers 60 each includes a gather sheet 62 continuously extending in the substantial width direction and elongated resilient and elastic members 63 that are stretched and fixed to the gather sheet 62 along the front-back direction. The gather sheet 62 may be composed of water-repellent non-woven fabric, and the elongated resilient and elastic members 63 may be composed of rubber thread or the like. A plurality of resilient and elastic members may be provided on each gather sheet 62 as illustrated in FIGS. 1 and 3. Alternatively, a single elongated resilient and elastic member may be provided on each gather sheet 62.

The internal surface of the gather sheet 62 has a fixation starting end in the width direction above the side part of the top sheet 30. The section residing outwards from the fixation starting end in the width direction is fixed with a hotmelt adhesive to a side part of the corresponding liquid impervious sheet 11 and the side part of the corresponding outer sheet 12 residing outwards from the side part of the liquid impervious sheet 11 in the width direction.

In an area surrounding each leg of the wearer, the inner side in the width direction of the fixation starting end of the three-dimensional side gather 60 is fixed to the top sheet 30 at the both ends in the front-back direction of the diaper. On the other hand, the section between the both ends in the front-back direction is an unfixed free portion. The free portion erects due to the contraction force of the elongated resilient and elastic members 63. After the diaper is worn, the diaper fits to the body in the form of a boat shape. Thus, the contraction force of the elongated resilient and elastic members 63 effects the three-dimensional side gather 60 and causes the three-dimensional side gather 60 to erect and come into close contact with the circumference of the leg. This prevents side leakage from the circumference of the leg.

Alternative to that illustrated in the drawings, the both ends in the front-back direction of the inward section of the gather sheet 62 in the width direction may be fixed in a folded state having a side base portion that extends from the outward area to the inward area in the width direction and a forward portion that turns up toward the body of the wearer from the center side edge in the width direction of the side base portion to extend outwards in the width direction. The section between the both ends may be an unfixed free portion.

(Flat Gather)

Figure 2:
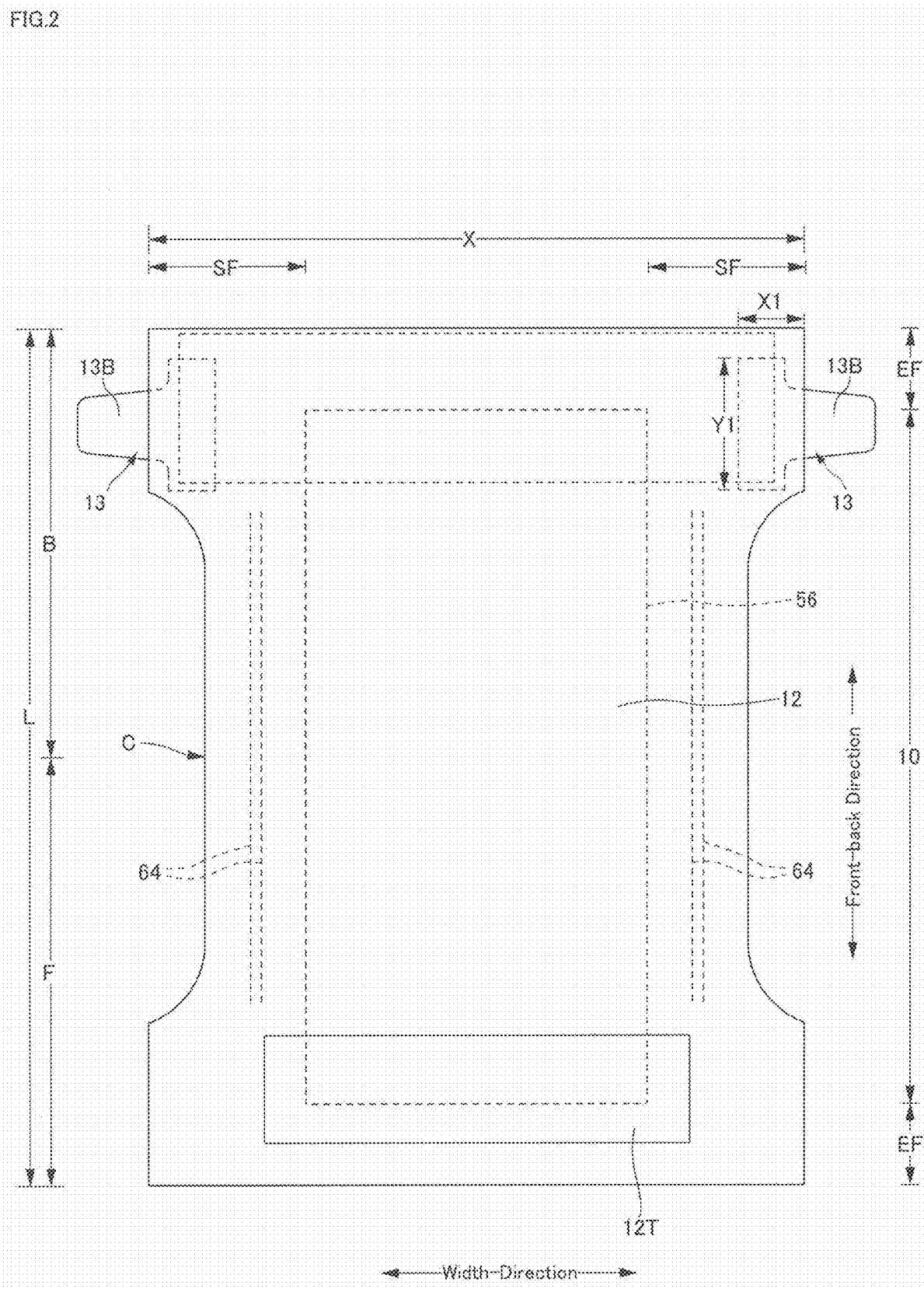
FIG. 2 is a plan view of the external surface of the tape-type unfolded disposable diaper.

With reference to FIGS. 1 to 3, in each of side flaps SF, SF, the leg-surrounding resilient and elastic members 64 composed of rubber threads or the like are stretched in the front-back direction and fixed between the respective gather sheet 62 and the liquid impervious sheet 11 outwards in the width direction of the fixed portions of the gather sheets 62 near the fixation starting end. In this way, the leg-surrounding portions of the side flap sections SF, SF serve as flat gathers. The leg-surrounding resilient and elastic members 64 may be disposed between the liquid impervious sheet 11 and the outer sheet 12 in the side flap sections SF. Two or more leg-surrounding resilient and elastic members 64 may be provided on each side as illustrated in the drawings. Alternatively, a single resilient and elastic member may be provided on each side.

(Absorbent Element)

The absorbent element 50 absorbs and retains liquid, such as urine and loose stool. The absorbent element 50 includes an absorber 56 and a package sheet 58 covering at least the back face and side faces of the absorber 56. The package sheet 58 may be omitted. The back face of the absorbent element 50 can be bonded to the internal surface of the liquid impervious sheet 11 with an adhesive, such as a hotmelt adhesive.

(Absorber)

The absorber 56 may be composed of a fiber assembly. Examples of the fiber assembly include fluff pulp, an assembly of short fibers, such as synthetic fibers, assembled through fiber stacking, and an assembly of filaments acquired through opening tows (fiber bundles) of synthetic fibers, such as cellulose acetate, as required. The fiber basis weight of fluff pulp or stacked short fibers may be within the range of approximately 100 to 300 g/m², and the fiber basis weight of a filament assembly may be within the range of approximately 30 to 120 g/m², for example. The fineness of synthetic fiber is within the range of 1 to 16 dtex, preferably 1 to 10 dtex, more preferably 1 to 5 dtex. Although the filaments in a filament assembly may be composed of non-crimped fiber, it should preferably be crimped fiber. The degree of crimp of crimped fiber is for example within the range of 5 to 75 per inch, preferably 10 to 50 per inch, more preferably 15 to 50 per inch. Uniformly crimped fiber is often used.

(Superabsorbent Polymer Particle)

Preferably, the absorber 56 is composed of superabsorbent polymer particles. More preferably, the superabsorbent polymer particles (SAP particles) are dispersed across the substantially entire thickness of the fiber assembly in at least the liquid receiving region.

If the SAP particles are absent or present in slight amounts in the upper, lower, or intermediate portions of the absorber 56, the SAP particles should not be referred to as being "dispersed across the entire thickness". The form in which the SAP particles are "dispersed across the entire thickness," includes the form in which the SAP particles are "uniformly" dispersed across the entire thickness of the fiber assembly, and the form in which the SAP particles are "unevenly" dispersed in the upper, lower, and intermediate portions but still dispersed in the upper, lower, and intermediate portions. The form in which the SAP particles are "dispersed across the entire thickness" does not exclude the form in which some of the SAP particles remain on the surface of the fiber assembly without intrusion into the fiber assembly or the form in which some of the SAP particles reside on the package sheet 58 after passing through the fiber assembly.

Superabsorbent polymer particles include "powder" in addition to "particles." The superabsorbent polymer particles may be the same as that of particles for general use in this type of absorbent article and preferably have a diameter of 1000 μm or less, more preferably 150 to 400 μm. There is no particular limitation on the material for the superabsorbent polymer particles. Preferably, the material has water absorption capacity of 40 g/g or more. Examples of the superabsorbent polymer particles are based on starch, cellulose, and synthetic polymer, such as graft copolymer of starch and acrylic acid (salt), saponified copolymers of starch and polyacrylonitrile, cross-linked sodium carboxymethyl cellulose, and acrylic acid (salt) copolymer. Preferably, the superabsorbent polymer particles are in the form of generally used particulate. Alternatively, the high absorbent polymer particles may have another form.

Preferably, the superabsorbent polymer particles have an absorption rate of 40 seconds or less. An absorption rate higher than 40 seconds causes ready so called reflowing of the liquid, which is more likely to flow back from the absorber 56 to the outside of the absorber 56.

The basis weight of the superabsorbent polymer particles can be appropriately determined in accordance with the required absorption volume of the absorber 56 depending on use. Although the basis weight depends on the use, it may be within the range of 50 to 350 g/m². A basis weight of polymers of less than 50 g/m² fails to achieve a sufficient absorption volume. A basis weight of polymers of more than 350 g/m² saturates the absorption volume and gives wearers a feeling of strangeness due to the granular texture generated by excess superabsorbent polymer particles.

(Package Sheet)

Examples of the material for the package sheet 58 include tissue paper, in particular, crepe paper, non-woven fabric, polyethylene laminated non-woven fabric, and a porous sheet. Preferably, the sheet is configured such that the superabsorbent polymer particles do not pass through the sheet. In the case where non-woven fabric is used in place of crepe paper, hydrophilic SMMS (spunbond/melt blown/melt blown/spunbond) non-woven fabric is preferred. Examples of the material thereof include polypropylene and polyethylene/polypropylene. The fiber basis weight is preferably within the range of 5 to 40 g/m², more preferably 10 to 30 g/m².

With reference to FIG. 3, the package sheet 58 may cover the entire absorber 56. Alternatively, the package sheet 58 may cover only the back face and side faces of the absorber 56. Alternatively, the upper and side faces of the absorber 56 may be covered with crepe paper or non-woven fabric while the lower face is covered with a liquid impervious sheet, such as a polyethylene sheet, although not illustrated. Alternatively, the upper face of the absorber 56 may be covered with crepe paper or non-woven fabric while the side and lower faces of the absorber 56 may be covered with a liquid impervious sheet, such as a polyethylene sheet. These materials function as the components of the package sheet. If required, the absorber 56 may be disposed between upper and lower sheets or on only the lower face of the package sheet 58. Such configurations are not preferred because they cannot block moving of the superabsorbent polymer particles.

(Fastening Tape)

Figure 7:
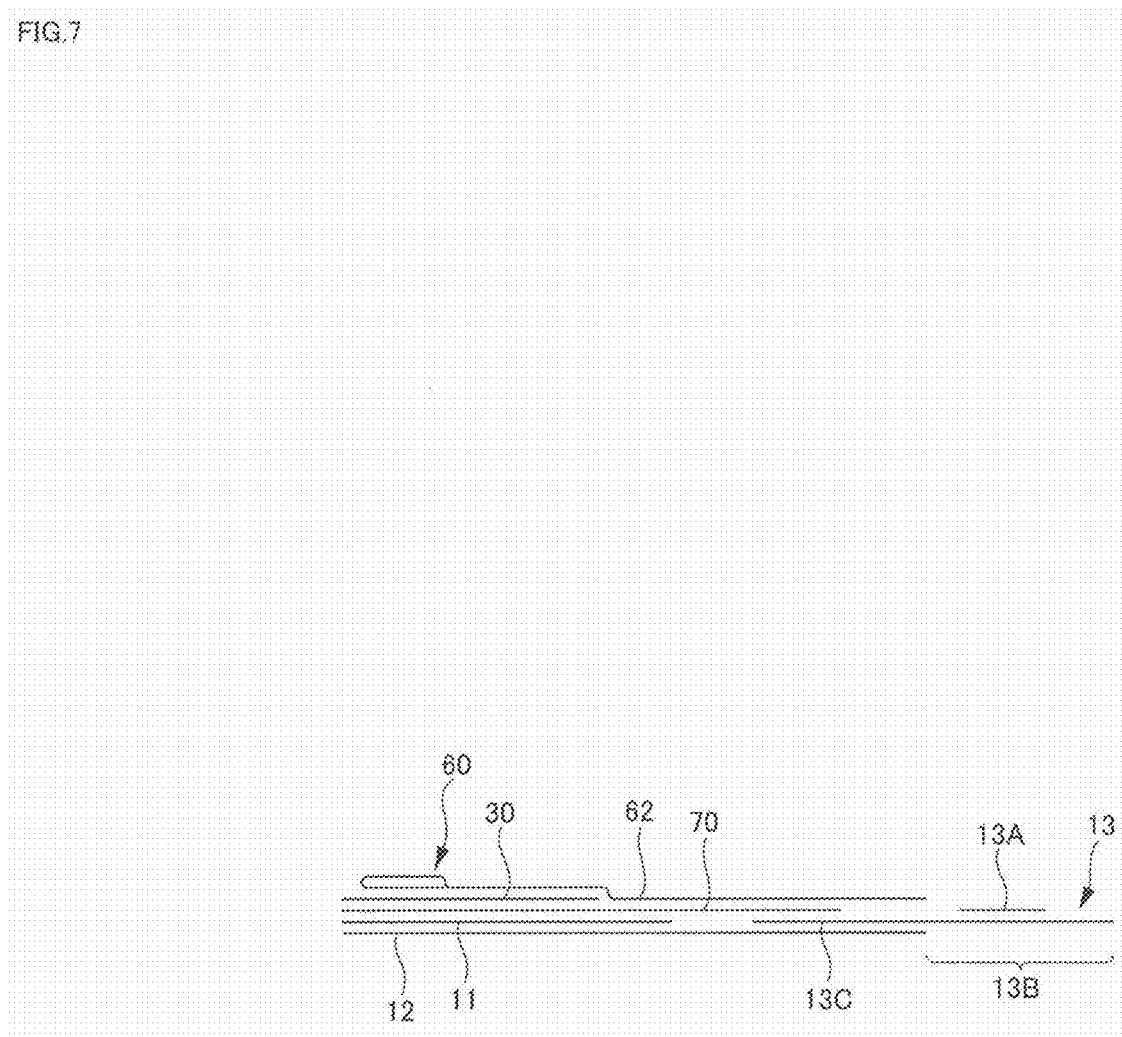
FIG. 7 is a cross-sectional view taken along line 5-5 in FIG. 1.

With reference to FIGS. 1, 2, and 7, the fastening tapes 13 each includes a tape attachment section 13C fixed to the corresponding side part of the diaper, a sheet base or tape main unit section 13B protruding from the tape attachment section 13C, and an engage portion 13A disposed in the intermediate portion in the width direction of the sheet base of the tape main unit section 13B relative to the ventral side. A portion of the fastening tape 13 from the tip to the engage portion 13A serves as a tab part. The tape attachment section 13C of the fastening tape 13 is disposed between the corresponding gather sheet 62 serving as an inner layer of the side flap section and the outer sheet 12 serving as the external layer, and bonded to the sheets 62 and 12 with a hotmelt adhesive. The engage portion 13A is bonded to the sheet base with an adhesive in an unpeelable manner.

A baby diaper has the following dimensions of the tape attachment section 13C: the length X1 in the width direction of the diaper is preferably within the range of 10 to 50 mm, more preferably 20 to 40 mm, and the length Y1 in the front-back direction is preferably within the range of 20 to 100 mm, more preferably 40 to 80 mm. The dimensions of the tape main unit section 13B are as follows: the length in the width direction of the diaper is preferably within the range of 30 to 80 mm, more preferably 40 to 60 mm, and the length (height) in the front-back direction is preferably within the range of 20 to 70 mm, more preferably 25 to 50 mm. The fastening tape 13 may be entirely or partly almost tapered, for example. If the length in the front-back direction and/or the length in the width direction are not constant, the ranges of the dimensions mentioned above are determined by averages. The fastening tape 13 may have a symmetrical shape, such as rectangular. Preferably, the fastening tape 13 is T-shaped in which the tape attachment section 13C has a large width and the tape main unit section 13B is tapered toward the tip. A user can easily hold the tab part of the tape main unit section 13B while tension can be applied in a large area between the left and right tape attachment sections 13C.

A preferred example of the engage portion 13A includes a hook member of a mechanical fastener (hook and loop fastener). The hook member includes many engagement projections on the external surface side. The engagement projections may have any one of the following shapes: (A) a check mark shape; (B) a J shape; (C) a mushroom shape; (D) a T shape; and (E) a double J shape (two J shaped engagement protrusions bonded together by their back faces). Alternatively, an adhesive layer may be provided as the engage portion of the fastening tape 13.

The sheet base of the tape attachment section and the tape main unit section may be composed of non-woven fabric, a plastic film, polyethylene laminated non-woven fabric, paper, or a composite material of these materials. Preferred are spunbonded non-woven fabric, air through non-woven fabric, and spunlaced non-woven fabric having a fineness within the range of 1.0 to 3.5 dtex, a basis weight within the range of 20 to 100 g/m$^2$, and a thickness of 1 mm or less.

To wear the diaper, the dorsal side flap sections SF are overlapped with the outer side of the ventral side flap sections SF and the fastening tapes are engaged at appropriate sites on the external surface of the ventral side F. The engage positions and dimensions of the fastening tapes 13 may be arbitrarily decided. For a baby diaper, the engagement site is positioned within a rectangular area having a length in the front-back direction within the range of 20 to 80 mm, a length in the width direction within the range of 150 to 300 mm, and a length in the height direction between the edge of the upper end and the edge of ventral side within the range of 0 to 60 mm, preferably 20 to 50 mm, the rectangular area preferably being disposed in the central area in the width direction of the diaper.

Preferably, the tape attachment sections 13C of the fastening tapes 13 are attached such that the tape attachment sections 13C of the fastening tapes 13 overlap at the boundary between the dorsal-side end flap section EF and the absorbent element 50 because the tension applied after the diaper is worn, between the tape attachment sections 13C of the left and right fastening tapes 13 firmly pushes the dorsal side end part (back end part) of the absorbent element 50 against the body of the wearer. If the tape attachment sections 13C of the fastening tapes 13 are disposed too far away from the dorsal side end part (back end part) of the diaper, the tension applied after the diaper is worn, between the right and left tape attachment sections 13C of the fastening tapes 13 fails to reach the dorsal side end part of the diaper and readily causes a gap to form between the dorsal side end part of the diaper and the surface of the body of the wearer. Thus, it is preferred that the length of the dorsal-side end flap section EF in the front-back direction be smaller than or equal to the length of the tape attachment sections 13C of the fastening tapes 13 in the front-back direction.

(Target Sheet)

Preferably, the engagement sites of the fastening tapes 13 on the ventral side F have a target sheet 12T having targets to facilitate the engagement. In the case where the engage portion 13A is a hook member, the target sheet 12T may include a sheet base composed of plastic film or non-woven fabric with many looped threads provided on the surface thereof that are caught by the engagement projections of the hook member. In the case where the engagement portion is an adhesive layer, the target sheet 12T may include a sheet base composed of a sticky plastic film having a stripped smooth surface. In the case where the engage portion of the fastening tapes 13 on the ventral side F, for example, the outer sheet 12 illustrated in the drawings is composed of non-woven fabric and the engagement portion 13A of the fastening tapes 13 is the hook member, the target sheet 12T may be omitted so that the hook member 13A engages with the non-woven fabric of the outer sheet 12. In such a case, the target sheet 12T may be disposed between the outer sheet 12 and the liquid impervious sheet 11.

(End Flap Section)

The end flap sections EF extend from the front and back sides of the main absorbent unit section 10 exclusive of the absorbent element 50. The extended section on the front side is the ventral-side end flap section EF, and the extended section on the back side is the dorsal-side end flap section EF.

For the same reason as that described above, the length of the dorsal-side end flap section EF in the front-back direction is preferably smaller than or equal to the length of the attachment of the fastening tapes 13 in the front-back direction and preferably 10 mm or more. If the dorsal side end part of the diaper is too close to the absorbent element 50, the thickness and elasticity of the absorbent element 50 cause a gap to form between the dorsal side end part of the diaper and the surface of the body of the wearer.

The length of each of the ventral-side end flap section EF and the dorsal-side end flap section EF in the front-back direction is preferably within the range of approximately 5% to 20% of the entire length L of the diaper in the front-back direction, and for a baby diaper, the length is within the range of 10 to 60 mm, preferably 20 to 50 mm.

(Dorsal Side Stretchable Waist Sheet)

Figure 5:
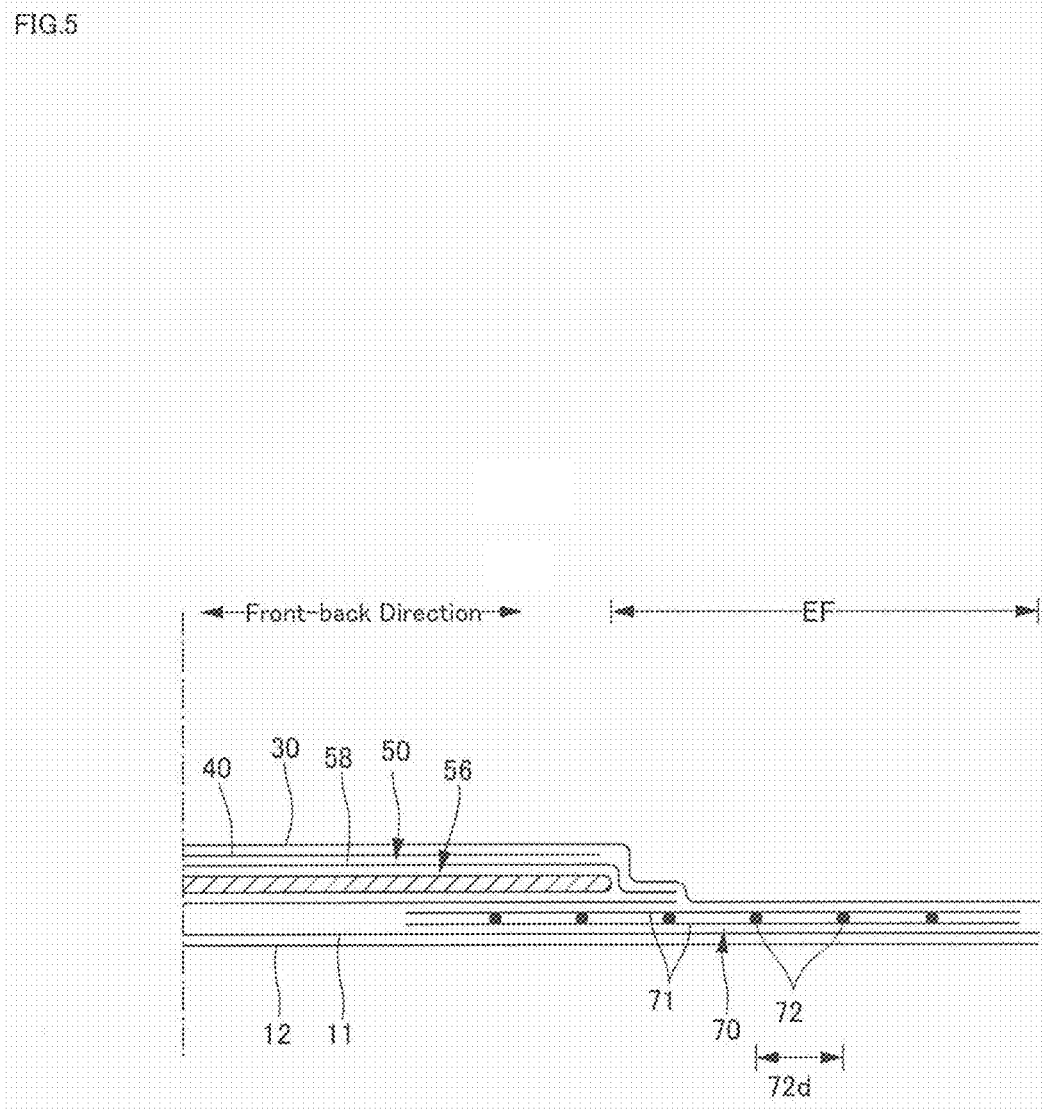
FIG. 5 is a cross-sectional view taken along line 8-8 in FIG. 1.
Figure 6:
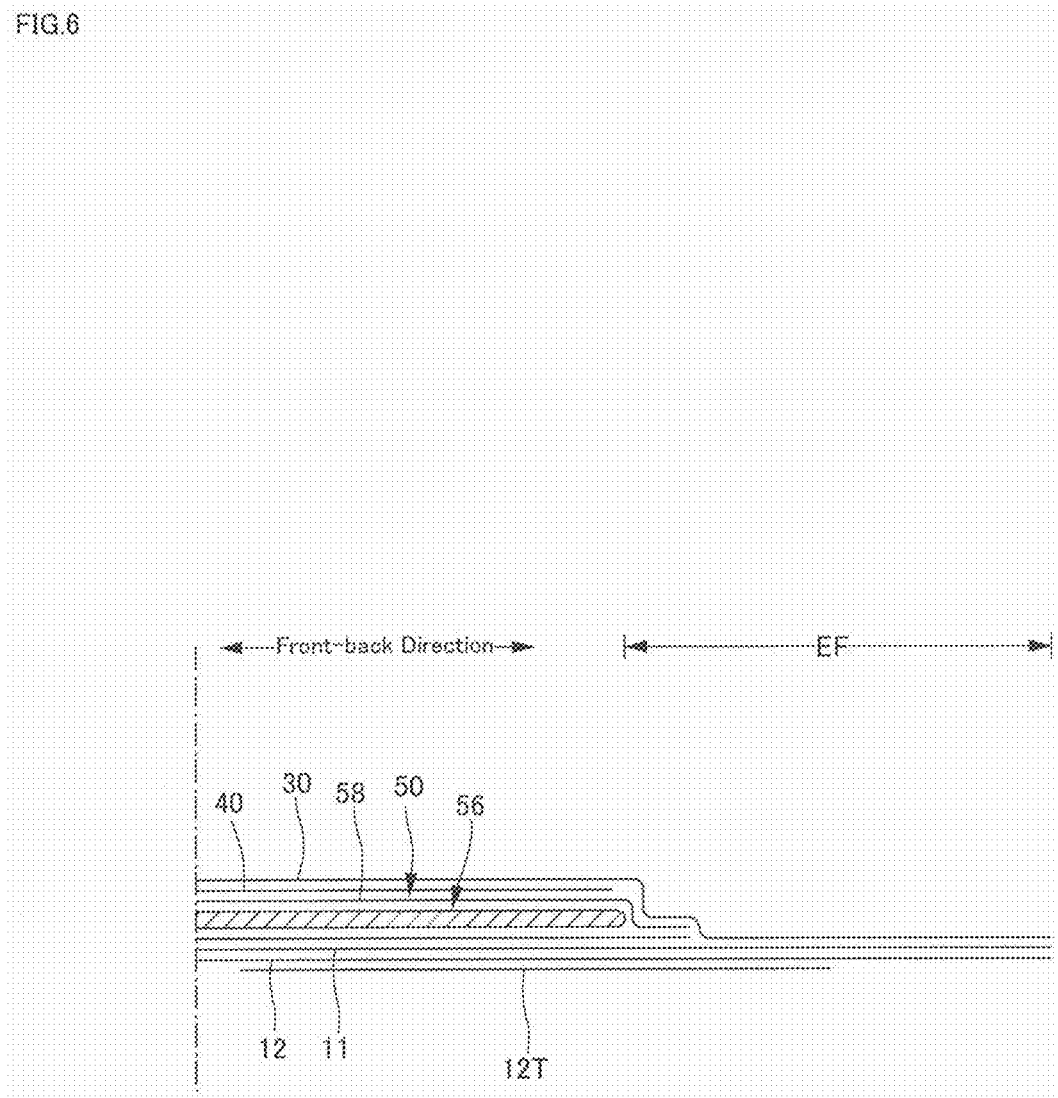
FIG. 6 is a cross-sectional view taken along line 9-9 in FIG. 1.

A band-like dorsal side stretchable waist sheet 70 that is elastically stretchable/contractable in the width direction is provided between the both fastening tapes 13, to enhance the fit of the dorsal side section of the diaper, as illustrated in the drawings. Preferably, the both ends of the dorsal side stretchable waist sheet 70 extend to the sites overlapping the attachment parts of the fastening tapes 13. Alternatively, the both ends of the dorsal side stretchable waist sheet 70 may be disposed in the central side in the width direction apart from the attachment parts of the fastening tapes 13. An appropriate length of the dorsal side stretchable waist sheet 70 in the front-back direction is approximately the same length as the attachment parts of the fastening tapes 13 in the front-back direction. A difference of approximately ±20% is acceptable. Preferably, the dorsal side stretchable waist sheet 70 overlaps the boundaries between the dorsal-side end flap section EF and the absorbent element 50, as illustrated in the drawings, so that the dorsal side end of the absorbent element 50 is firmly urged to the body of the wearer. The dorsal side stretchable waist sheet 70 may be an elastic sheet, such as a rubber sheet. Non-woven fabric or paper is suitable for air permeability. In such a case, the elastic sheet may be composed of stretchable non-woven fabric having air permeability. Preferably, the dorsal side stretchable waist sheet 70 is preferably formed by bonding two sheet bases 71 composed of non-woven fabric with an adhesive, such as a hotmelt adhesive, and stretched and fixed resilient and elastic members 72 in the forms of porous sheets, nets, or elongated members (threads or strings) disposed between the sheet bases 71 along the width direction between the two sheet bases 71, as illustrated in FIG. 5. In such a case, the sheet bases 71 may have the same configuration as that of the outer sheet 12. The extension ratio of the resilient and elastic members 72 is preferably within the range of approximately 150% to 250%. In the case of the resilient and elastic members 72 in the forms of elongated members (threads or strings), it is preferred that 5 to 15 resilient and elastic members 72 having a thickness in the range of 420 to 1120 dtex be disposed at a pitch 72$d$ of 3 to 10 mm.

Preferably, some of the resilient and elastic members 72 are preferably disposed across the absorbent element 50, as illustrated in the drawing, to enhance the fit of the absorbent element 50. In such a case, the resilient and elastic members 72 overlapping the absorbent element 50 may be partially or entirely cut to be isolated from the effect of a contraction force. This prevents the contraction of the dorsal side end part of the absorbent element 50 in the width direction and enhances the fit.

The resilient and elastic members 72 may be fixed along the entire length of the sheet bases 71 in the longitudinal direction of the sheets (the width direction of the diaper). Preferably, the resilient and elastic members 72 should be absent or treated so as not to exert contraction force in areas approximately 5 to 20 mm from the ends of sheets in the front-back direction (width direction of the diaper) to be isolated from a contraction force and avoid shrinkage or roll-up in these areas during attachment to the diaper body.

The dorsal side stretchable waist sheet 70 is disposed between the gather sheets 62 and the outer sheets 12 at the both sides of the liquid impervious sheet 11 in the width direction and between the liquid impervious sheet 11 and the absorbent element 50 in the site in which the dorsal side stretchable waist sheet 70 overlaps the liquid impervious sheet 11, as illustrated in the drawing. Alternatively, the dorsal side stretchable waist sheet 70 may be disposed between the liquid impervious sheet 11 and the outer sheet 12, on the external surface of the outer sheet 12, or between the top sheet 30 and the absorbent element 50. Alternatively, the dorsal side stretchable waist sheet 70 may be disposed on the top sheet 30. In such a case, the dorsal side stretchable waist sheet 70 may be disposed on the gather sheets 62 at both sides of the liquid impervious sheet 11 in the width direction. In the case where the outer sheet 12 is composed of a plurality of sheet bases, the entire dorsal side stretchable waist sheet 70 may be disposed between the sheet bases of the outer sheet 12.

(Extruded Protrusion of Top Sheet)

Figure 8:
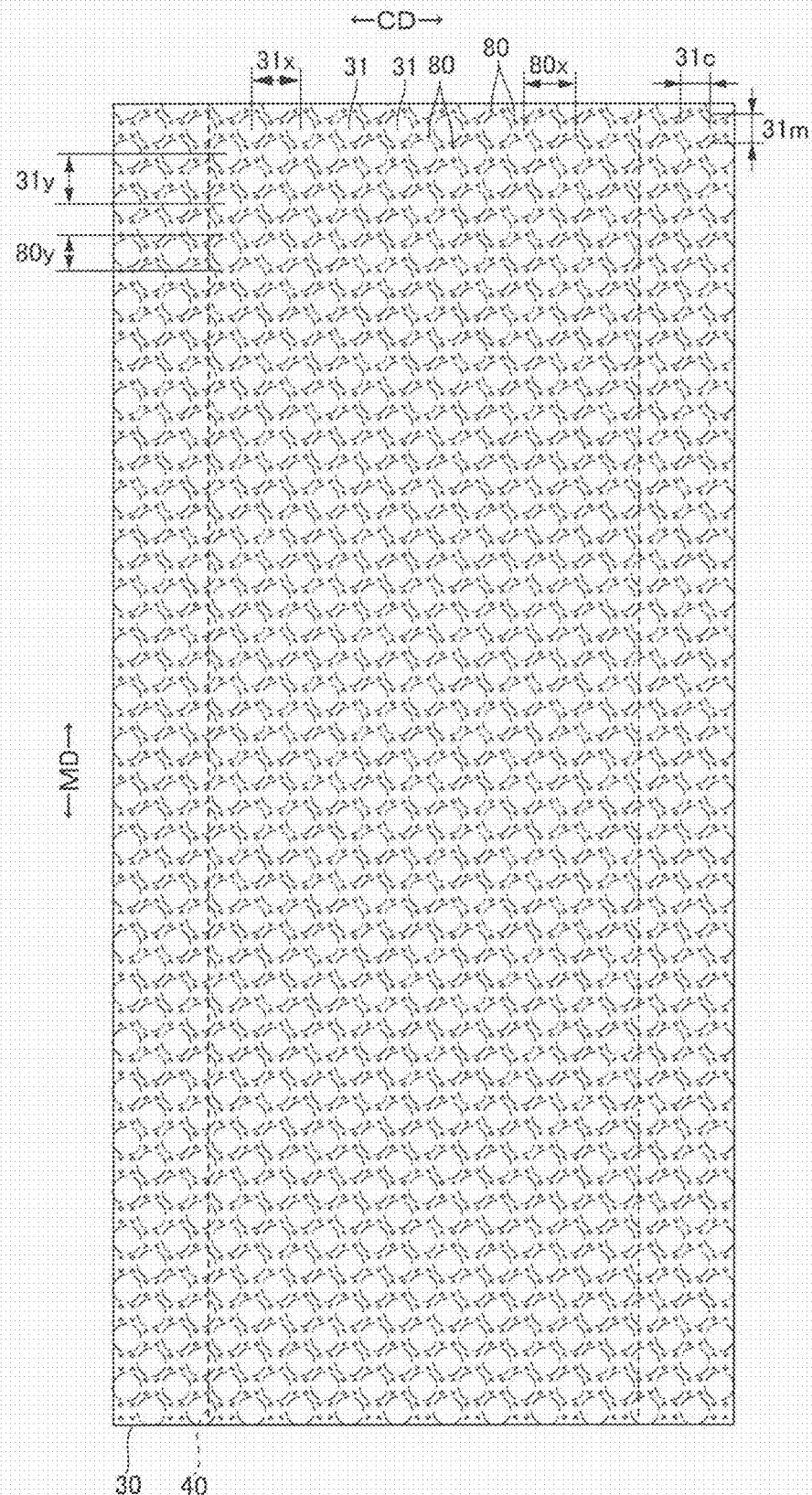
FIG. 8 is a plan view of a top sheet and a second sheet.
Figure 9:
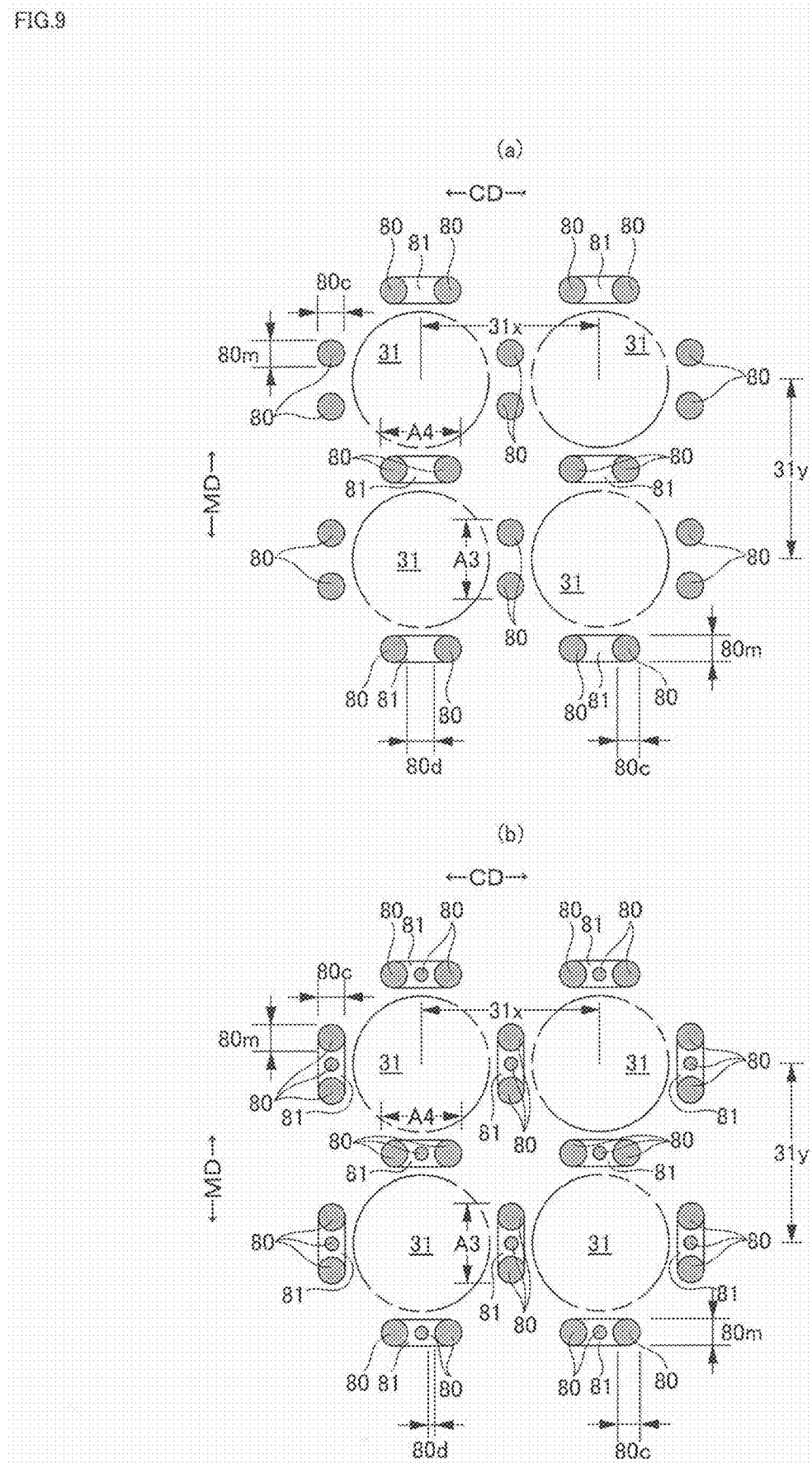
FIGS. 9(a) and 9(b) are enlarged plan views of bonding patterns of the bonded portions of the top sheet and the second sheet.
Figure 10:
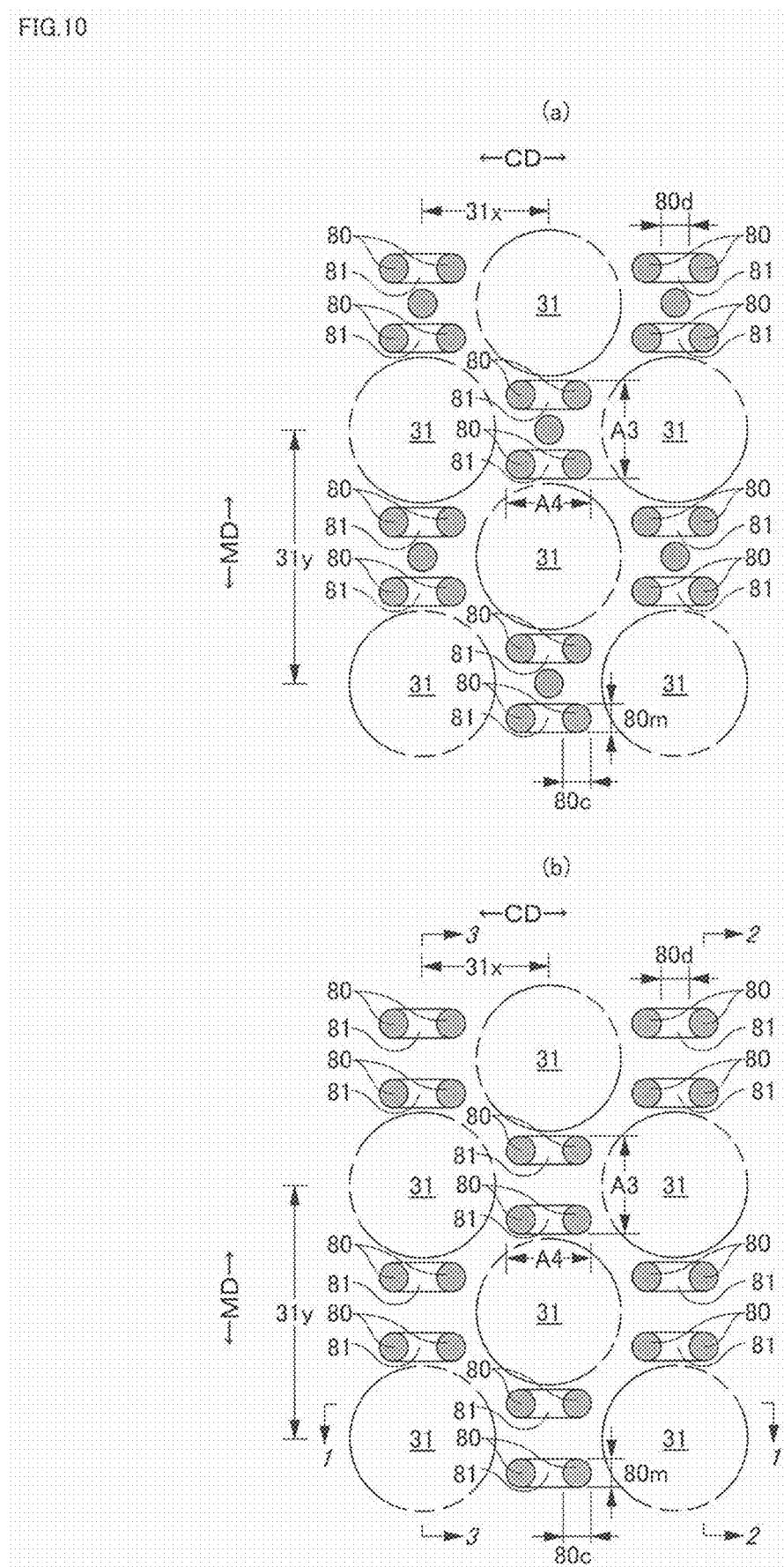
FIGS. 10(a) and 10(b) are enlarged plan views of bonding patterns of the bonded portions of the top sheet and the second sheet.
Figure 11:
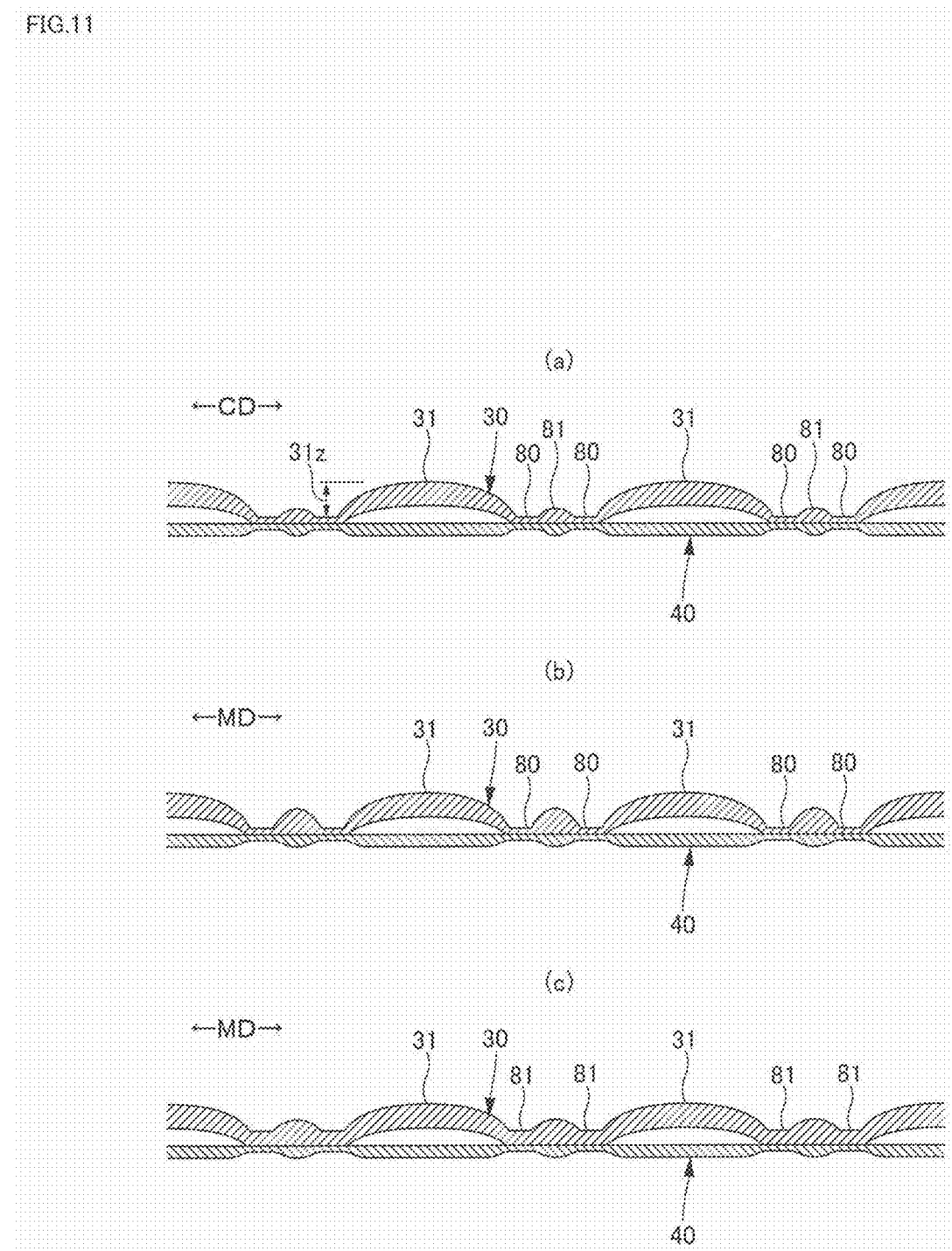
FIGS. 11(a), 11(b) and 11(c) are cross-sectional views taken along lines 1-1, 2-2, and 3-3 in FIG. 10(b).

The top sheet 30 has a large number of extruded protrusions 31, which is embossed from the back side to the front side and disposed at intervals in the width direction and front-back direction. The extruded protrusions 31 may be appropriately disposed in a matrix pattern, as illustrated in FIG. 9, or in a staggered pattern (in which adjacent rows are staggered), as illustrated in FIGS. 8 and 10.

The dimensions of the extruded protrusions 31 may be arbitrarily decided. For example, the length 31$m$ of the extruded protrusion 31 in the MD is smaller than or equal to the pitch 80$y$ between the center of a top-second bonded portion 80 positioned at one side in the MD of the extruded protrusion 31 (described below) and the center of a top-second bonded portion 80 positioned at the other side in the MD of the extruded protrusion 31, as illustrated in FIGS. 8 to 11. Preferably, the low limit be approximately 0.9 times the pitch 80$y$. Preferably, the length 31$m$ is within the range of approximately 2.7 to 9 mm for a baby diaper. Similarly, the length 31$c$ of the extruded protrusion 31 in the CD is smaller than or equal to the pitch 80$x$ between the center of a top-second bonded portion 80 positioned at one side in the CD of the extruded protrusion 31 and the center of a top-second bonded portion 80 positioned at the other side in the CD of the extruded protrusion 31. Preferably, the low limit is approximately 0.9 times the pitch 80$x$. Preferably, the length 31$c$ is within the range of approximately 2.7 to 9 mm for a baby diaper. The extruded protrusions 31 preferably has a height 31$z$ within the range of approximately 0.8 to 2 mm for a baby diaper.

The "MD" and "CD" of a product respectively refer to the "MD" and "CD" of the processing equipment of the extruded protrusions 31, one corresponding to the front-back direction while the other corresponding to the width direction. The MD of the product is the direction of the orientation of the fibers in the non-woven fabric of the top sheet 30. The orientation of fiber is the extending direction of the fibers in the non-woven fabric. The orientation of fiber can be determined through a testing method in accordance with TAPPI Standard Method T481 for testing fiber orientation with zero-span tensile strength or a simple scheme for determining fiber orientation by the ratio of tensile strengths in the front-back direction to the with direction. For the absorbent article illustrated in the drawing, the front-back direction corresponds to the MD and the width direction corresponds to the CD, like most absorbent articles.

The extruded protrusions 31 can be disposed at an appropriate interval. For a baby diaper having a matrix pattern as illustrated in FIG. 9, preferably, the CD pitch 31$x$ of the MD rows of extruded protrusions 31 adjacent each other in the CD is within the range of approximately 3 to 10 mm, and the MD pitch 31$y$ of the CD rows of extruded protrusions 31 adjacent each other in the MD is within the range of approximately 3 to 10 mm. For a staggered pattern, as illustrated in FIGS. 8 and 10, preferably, the CD pitch 31$x$ of the MD rows of extruded protrusions 31 adjacent each other in the CD is within the range of approximately 3 to 10 mm, and the MD pitch 31$y$ of the CD rows of extruded protrusions 31 adjacent each other in the MD is within the range of approximately 3 to 10 mm.

Preferably, the extruded protrusions 31 have a shape of a circular dome. Alternatively, the extruded protrusions 31 may have a shape of an elliptical dome or a polygonal dome. The extruded protrusions 31 are formed through embossing of the top sheet 30. Thus, the shape of the convexes used for the embossing may be appropriately modified into a desired shape.

(Top-Second Bonded Portion)

With reference to FIGS. 8, 10(*b*), 11, and 13, the regions between the extruded protrusions 31 in the top sheet 30 adjacent each other in the width direction and the front-back direction are pressure welded to the second sheet 40, to forma large number of top-second bonded portions 80 arrayed in an intermittent bonding pattern in the width direction and the front-back direction. Such row is characterized in that the bonding pattern of the top sheet 30 and the second sheet 40 includes rows of the plurality of top-second bonded portions 80 disposed at intervals in the CD in the regions between the extruded protrusions 31 adjacent each other in the MD so as to be provided across the center positions in the CD of the regions. Furthermore, the areas between the top-second bonded portions 80 in the rows in the CD define compressed portions 81 in which the top sheet 30 and the second sheet 40 are unwelded and the top sheet 30 is more highly compressed compared to the areas at both sides of the compressed portions 81 in the MD. In the compressed portions 81, the top sheet 30 may be compressed together with or without the second sheet 40 as long as the top sheet 30 is compressed. In the areas other than the top-second bonded portions 80 and the compressed portions 81, the top sheet 30 and the second sheet 40 may be unwelded and compressed as in the areas between the top-second bonded portions 80 in the CD. Preferably, the top sheet 30 and the second sheet 40 are unwelded and the top sheet 30 is less compressed than the areas between the top-second bonded portions 80 in the CD (or not compressed at all). That is, T1<T2=T3 is allowable while T1<T2<T3 is preferred, where in the top sheet 30, T1 is the thickness of the top-second bonded portions 80, T2 is the thickness of the compressed portions 81, and T3 is the thickness of the areas other than the top-second bonded portions 80 and the compressed portions 81.

Figure 13:
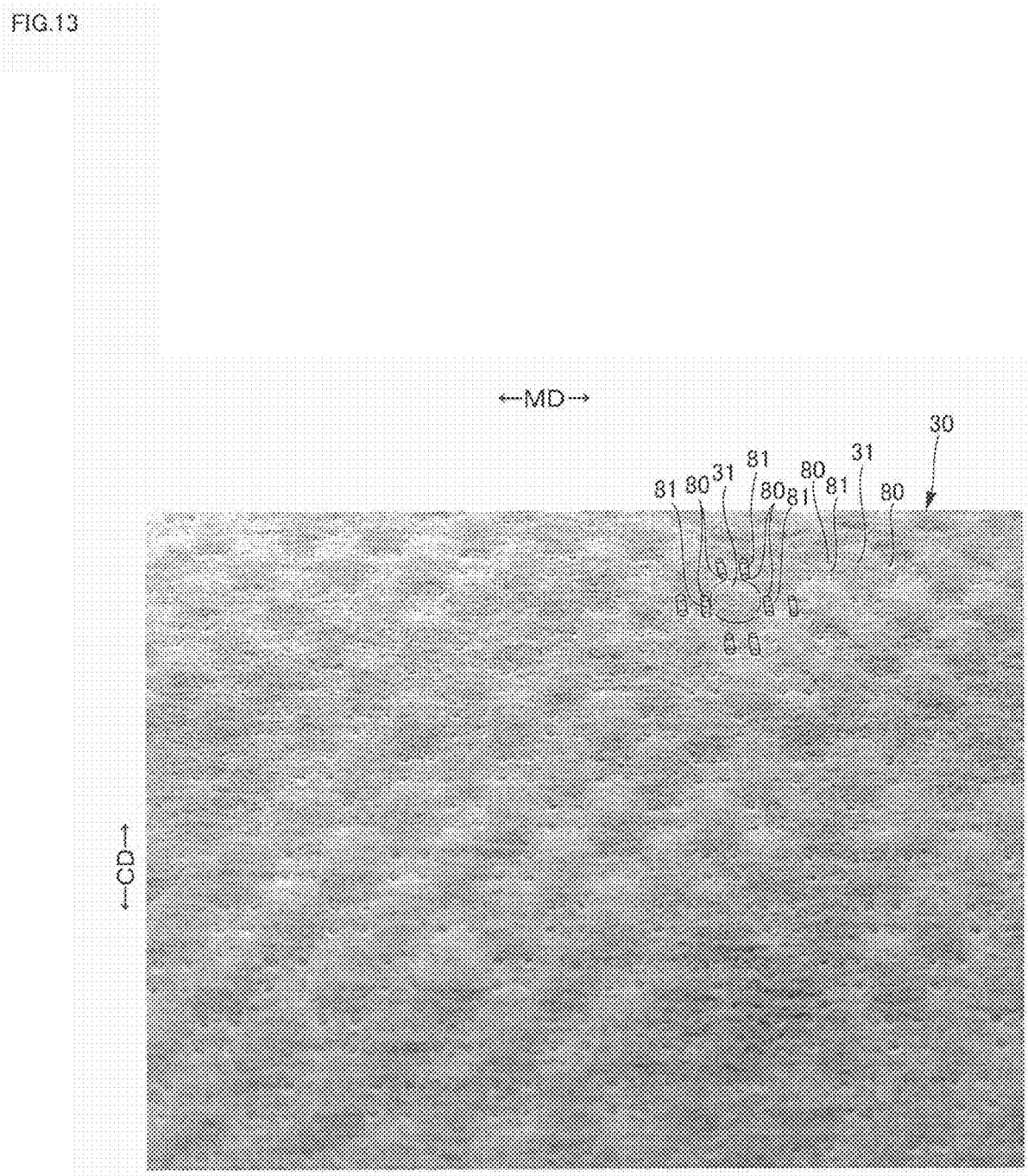
FIG. 13 is a photograph taken from substantially above an assembly of the top sheet and the second sheet.
Figure 14:
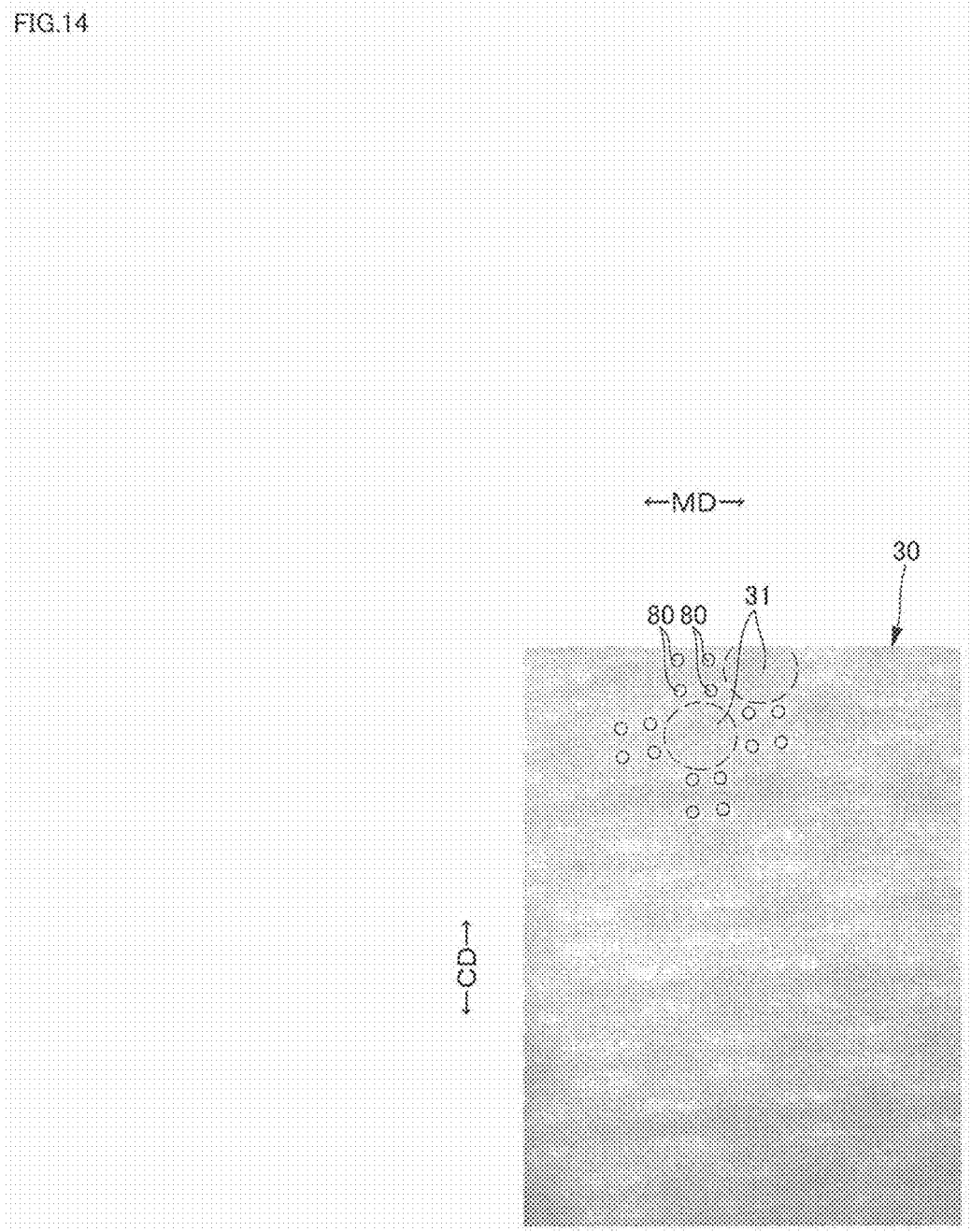
FIG. 14 is a photograph of the front surface of a comparative sample of a top sheet.

FIG. 13 illustrates a photograph of a sample assembly of the top sheet 30 and the second sheet 40 having the pattern illustrated in FIGS. 8 and 10(b). By bonding the top sheet 30 and the second sheet 40 in the characteristic bonding pattern of the areas between the extruded protrusions 31 adjacent each other in the MD, the pressure-welded top-second bonded portions 80 and the unwelded compressed portions 81 are formed such that they alternate in the CD and they are provided across vertical wrinkles that may form during formation of the extruded protrusions 31. Thus, the top-second bonded portions 80 can be formed while the vertical wrinkles are significantly stretch, and this stretched state can be maintained or substantially maintained even after production, as it is also apparent from a comparison of the sample according to the present invention illustrated in FIG. 13 with the comparative sample illustrated in FIG. 14. The bonded areas intermittently aligned in the CD establish adequate softness and satisfactory appearance. In contrast, the comparative sample including the top-second bonded portions 80 not satisfying the conditions described above cause many wrinkles along the MD at intervals in the CD, impairing the pleasing appearance.

There is no particular limitation on the bonding pattern as long as a plurality of top-second bonded portions 80 align at intervals in the CD in the regions between extruded protrusions 31 adjacent each other in the MD and the areas between the top-second bonded portions 80 in the CD define respective connected compressed portions 81. In consideration of wrinkle prevention, it is preferred that the top-second bonded portions 80 be provided between the extruded protrusions 31 adjacent each other in the MD at center positions in the CD corresponding to the center portions of the extruded protrusions 31 in the CD, as illustrated in FIGS. 9(a) and 10(a). Alternatively, it is preferred that top-second bonded portions 80 be absent at the center positions corresponding to the center portions of the extruded protrusions 31 in the CD, as illustrated in FIGS. 9(a) and 10(a), to enhance softness. In the former, it is preferred that the top-second bonded portion 80 provided at the center position has an area smaller than that of the other top-second bonded portion 80, in consideration of softness.

A single row of a plurality of top-second bonded portions 80 aligned in the CD at intervals is disposed in the region between the extruded protrusions 31 aligned in the MD, as illustrated in FIG. 9. Alternatively, a plurality of rows may be provided at intervals in the MD, as illustrated in FIGS. 8 and 10. The former is suitable for a pattern in which the extruded protrusions 31 are disposed in a matrix at a small pitch in the MD, as illustrated in FIG. 9. The latter is suitable for a pattern in which the extruded protrusions 31 are disposed in a staggered pattern at a large pitch in the MD, as illustrated in FIGS. 8 and 10. In the latter configuration, the top sheet 30 and the second sheet 40 in the areas between the top-second bonded portions 80 in the MD may be unwelded and compressed as in the areas between the top-second bonded portions 80 in the CD. Alternatively, the top sheet 30 and the second sheet 40 may be unwelded and the top sheet 30 may be more lightly compressed (or not compressed at all) in the areas between the top-second bonded portions 80 in the MD compared to the areas between the top-second bonded portions 80 in the CD, to enhance softness and appearance.

The top-second bonded portions may each have any shape. Other than the circle illustrated in the drawings, examples include ellipse, polygon, star, and cloud.

The top-second bonded portions 80 may be arbitrarily decided. Preferably, the top-second bonded portions 80 disposed between the extruded protrusions 31 adjacent each other in the MD have a dot shape in which the MD length 80m is approximately 0.1 to 0.4 times the MD pitch 31y of the CD rows of extruded protrusions 31 adjacent each other in the MD (within the range of 0.5 to 3 mm for baby diapers), and the CD length 80c is approximately 0.1 to 0.4 times the CD pitch 31x of the MD rows of extruded protrusions 31 adjacent each other in the CD (within the range of 0.5 to 3 mm for baby diapers). Preferably, the distance 80d between adjacent top-second bonded portions 80 in the CD is approximately 1 to 5 times the CD length 80c of the top-second bonded portions 80 (within the range of 0.5 to 15 mm for baby diapers), and approximately two to four top-second bonded portions 80 are disposed in a row in the CD.

For the extruded protrusions 31 disposed in a staggered pattern, the areas between the extruded protrusions 31 adjacent each other in the CD are shared by the corresponding extruded protrusions 31 adjacent each other in the MD and thus the top-second bonded portions 80 disposed between the extruded protrusions 31 adjacent each other in the CD are served as those between the corresponding extruded protrusions 31 adjacent each other in the MD, as illustrated in FIG. 10. Alternatively, for the extruded protrusions 31 disposed in a matrix, top-second bonded portions 80 disposed between the extruded protrusions 31 adjacent each other in the MD are different from those between the extruded protrusions 31 adjacent each other in the CD such that the top-second bonded portions 80 are intermittently aligned in the MD, as illustrated in FIG. 9. There is no particular limitation on the pattern in which top-second bonded portions 80 disposed between the extruded protrusions 31 adjacent each other in the CD are disposed. Preferably, the top-second bonded portions 80 having a dot shape are aligned in the MD at intervals. Similar to the areas between the top-second bonded portions 80 adjacent each other in the CD, also in the areas between the top-second bonded portions 80 aligned adjacent each other in the MD, the compressed portions 81 may be formed, as illustrated in FIG. 9(b). A single MD row of top-second bonded portions 80 may be disposed midway between the extruded protrusions 31 adjacent each other in the CD, as illustrated in the drawing. Alternatively, a plurality of rows may be disposed at intervals in the CD. There is no particular limitation on the dimension of the dot-shaped top-second bonded portion 80. Preferably, the MD length 80m is approximately 0.1 to 0.4 times the MD center pitch 31y of the CD rows of the extruded protrusions 31 adjacent each other in the MD (within the range of 0.5 to 3 mm for baby diapers), and the CD length 80c is approximately 0.1 to 0.4 times the CD center pitch 31x of the MD rows of extruded protrusions 31 adjacent each other in the CD (within the range of 0.5 to 3 mm for baby diapers).

The top-second bonded portions 80 are provided in an intermittent bonding pattern along the width direction and the front-back direction at intervals in both directions, which may be appropriately decided. For example, it is preferred that the CD bonding length A3 of the top-second bonded portions 80 disposed between extruded protrusions 31 adjacent each other in the MD be approximately 0.3 to 1 time the CD center pitch 31$x$ of the MD rows of extruded protrusions 31 adjacent each other in the CD (within the range of 1 to 10 mm for baby diapers), and the MD bonding length A4 of the top-second bonded portions 80 disposed between extruded protrusions 31 adjacent each other in the CD be approximately 0.3 to 1 time the MD center pitch 31$y$ of the CD rows of extruded protrusions 31 adjacent each other in the MD (within the range of 1 to 10 mm for baby diapers). Excessively large CD bonding length A3 and MD bonding length A4 are equivalent to continuous top-second bonded portions 80 in the CD and MD. Thus, this may cause a reduction in the perviousness and softness of the top sheet 30.

<Exemplary Method of Producing Disposable Diaper>

Figure 12:
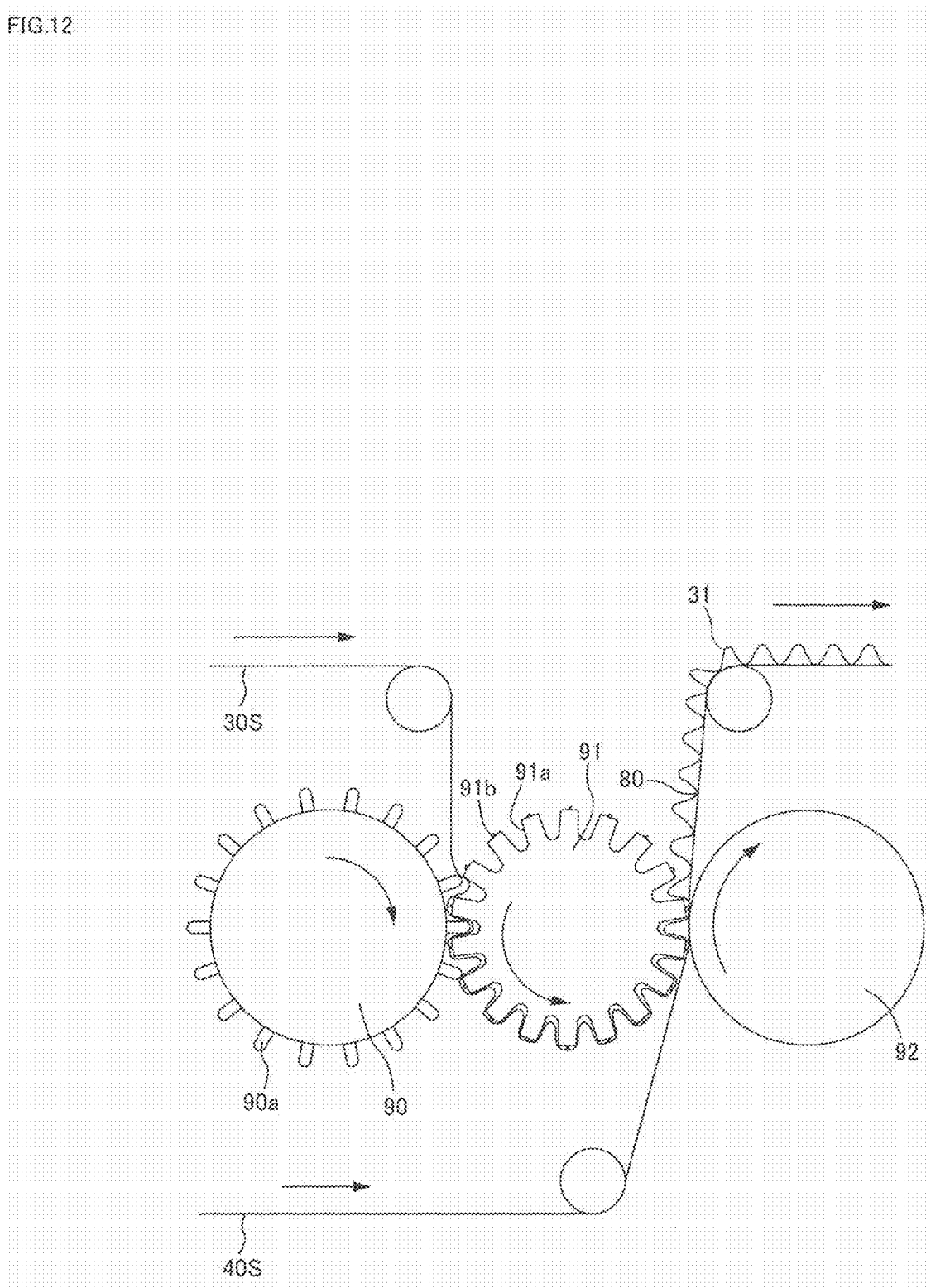
FIG. 12 illustrates an example assembling equipment of the top sheet and the second sheet.

FIG. 12 illustrates processing equipment of the top sheet 30 and the second sheet 40 for producing the disposable diaper described above. Specifically, the equipment includes a squeeze roll 90, a recessed roll 91 facing the squeeze roll 90, and a bonding roll 92 facing the recessed roll 91.

Figure 15:
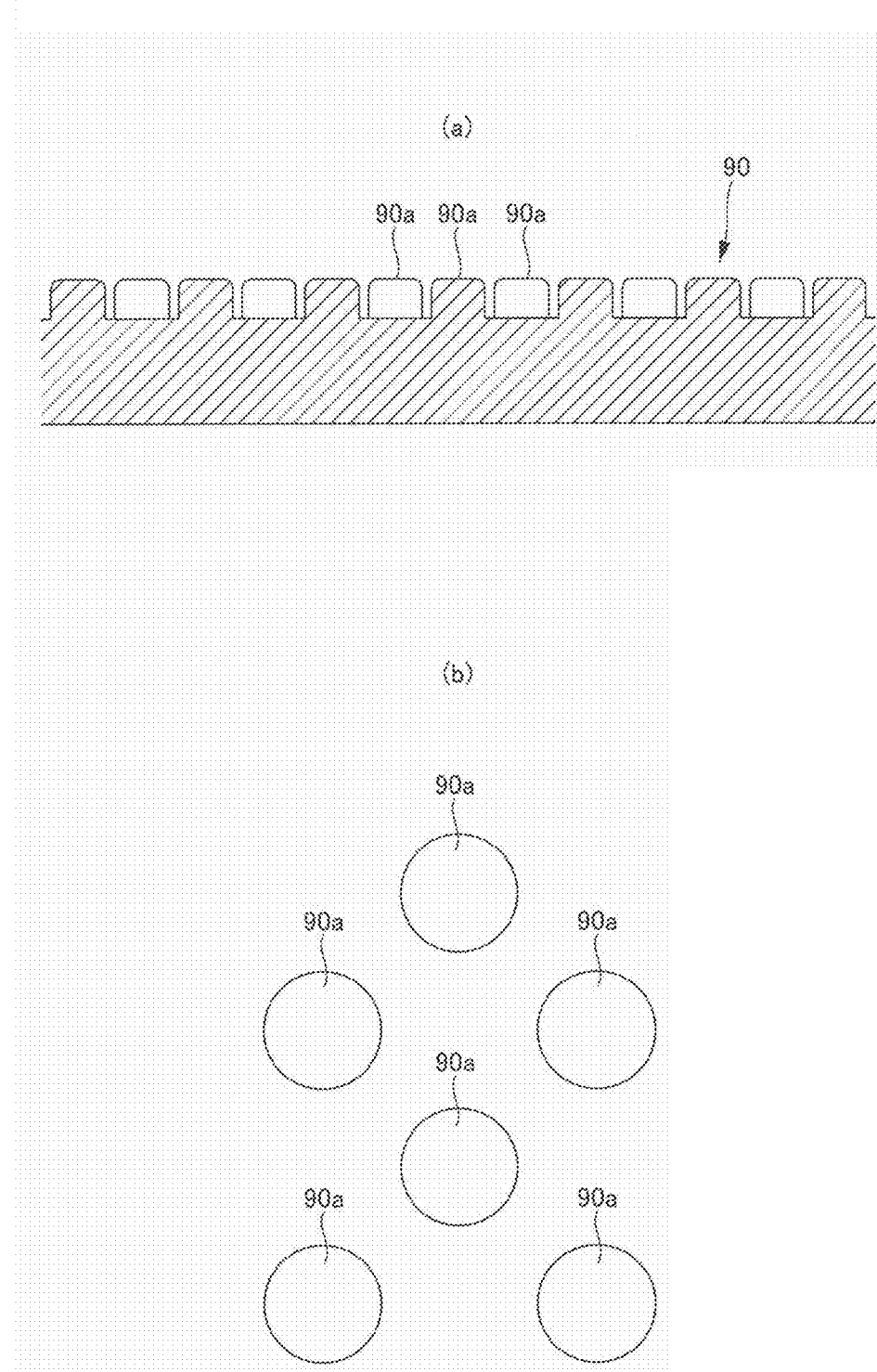
FIG. 15(a) is a cross-sectional view of an essential portion of a squeeze roll, and 15(b) is a development plan view of the circumferential face of the squeeze roll.

With reference to FIG. 15, the squeeze roll 90 has a large number of convexes 90$a$ disposed in a pattern of extruded protrusions 31 described above on its circumferential surface. The shape of the convexes of the squeeze roll 90 may be appropriately decided. Preferably, the convexes of the squeeze roll 90 have a shape of a circular truncated cone having a cross-section corresponding to the shape of the extruded protrusions 31 to be formed (for example, a circle, an ellipse, or a polygon).

Figure 16:
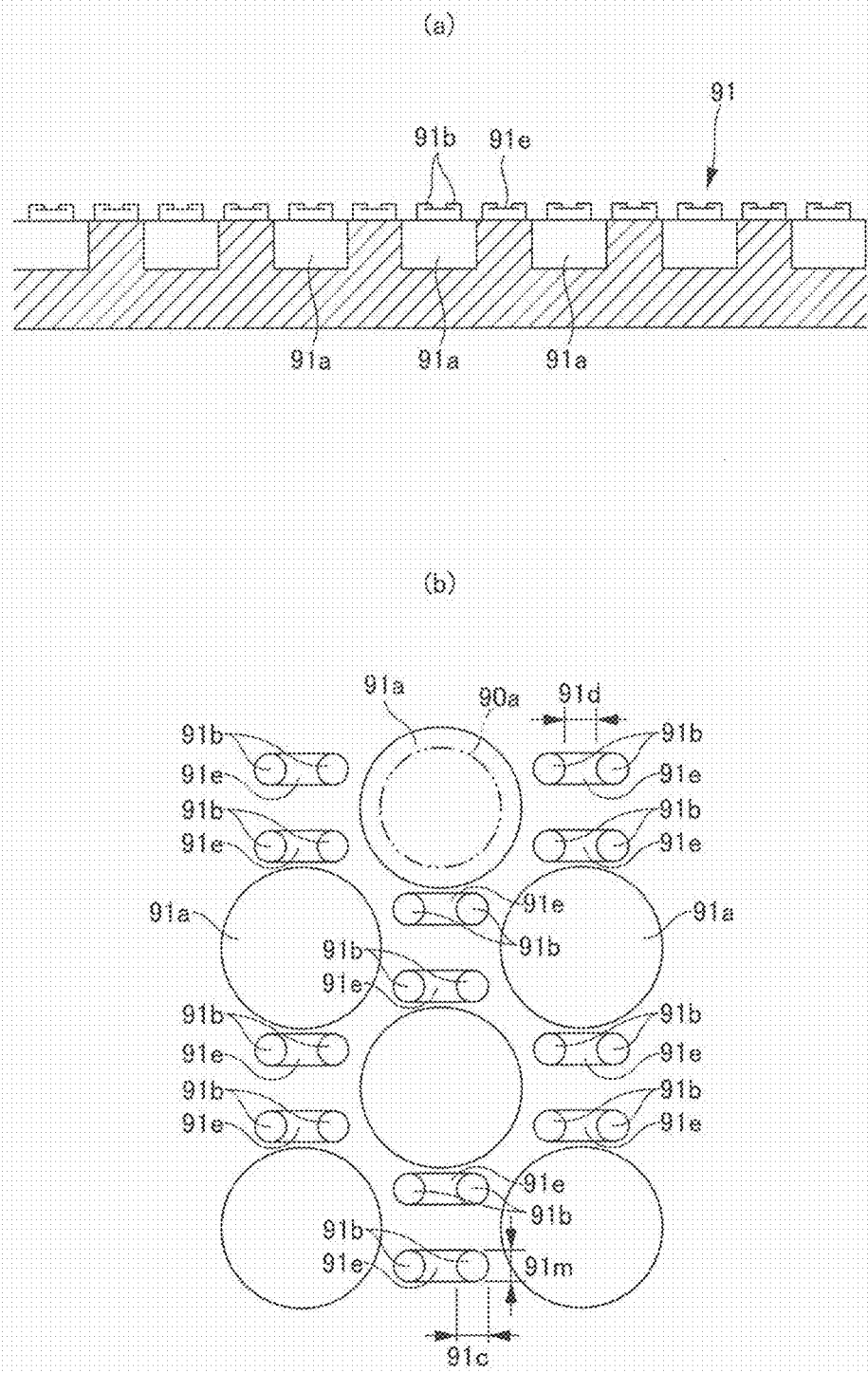
FIG. 16(a) is a cross-sectional view of an essential portion of a recessed roll.
FIG. 16(b) is a development plan view of the circumferential face of the recessed roll.

With reference to FIG. 16, the circumferential surface of the recessed roll 91 has concaves 91$a$ corresponding to the squeeze convexes 90$a$ of the squeeze roll 90. Bonding convexes 91$b$ and compression convexes 91$e$ are provided between adjacent concaves 91$a$. The bonding convexes 91$b$ form the top-second bonded portions 80 in the bonding pattern. The compression convexes 91$e$ compress the non-woven fabric 30S to be the top sheet 30 in the thickness direction without welding the top sheet 30 and the material 40S of the second sheet in the areas between the top-second bonded portions 80 in the CD. It should be appreciated that if the material 40S of the second sheet is a compressible material, such as non-woven fabric, in the thickness direction, the second sheet 40 is also compressed at the same time by the compression convexes 91$e$. In detail, the recessed roll 91 has a row of a plurality of bonding convexes 91$b$ aligned at intervals along the axial direction of the roll in each region between two adjacent convexes 90$a$ in the circumferential direction of the roll so as to be provided across the center positions of the region in the axial direction. The area between the bonding convexes 91$b$ in the axial direction in each region serves as the compression convex 91$e$. The areas other than the bonding convexes 91$b$, the compression convexes 91$e$, and the concaves 91$a$ do not compress the material. Alternatively, these areas may compress the material with a pressure approximately equal to or smaller than that applied by the compression convexes 91$e$. The concaves 91$a$ of the recessed roll 91 that form the protrusions in the material may be bottomless "through-holes" large enough to receive the respective convexes. In other words, "the concaves 91$a$" according to the present invention include "through-holes."

The dimensions, shape, and positions of the squeeze convexes 90$a$ of the squeeze roll 90 respectively correspond to the internal space dimensions, shape, and positions of the extruded protrusions 31 to be formed. The dimensions, shape, and positions of the concaves 91$a$ of the recessed roll 91 respectively correspond to the external dimensions, shape, and positions of the extruded protrusions 31 to be formed. The dimensions, shape, and positions of the bonding convexes 91$b$ of the recessed roll 91 respectively correspond to the dimensions, shape, and positions of the top-second bonded portions 80 to be formed. The dimensions, shape, and positions of compression convexes 91$e$ of the recessed roll 91 respectively correspond to the dimensions, shape, and positions of the compressed portions 81, if compressed portions 81 are to be formed. These dimensions, shape, and positions are modifiable as those of the extruded protrusions 31, the top-second bonded portions, and the compressed portions described above in the section on disposable diaper. The MD length 91$m$, the CD length 91$c$, and the CD pitch 91$d$ of the compression convexes 91$c$ in the configuration illustrated in FIG. 16($b$) may be defined within the same ranges of the MD length 80$m$, the CD length 80$c$, and the CD pitch 80$d$, respectively, of the top-second bonded portions 80 in the configuration illustrated in FIG. 10($b$), for example.

Figure 17:
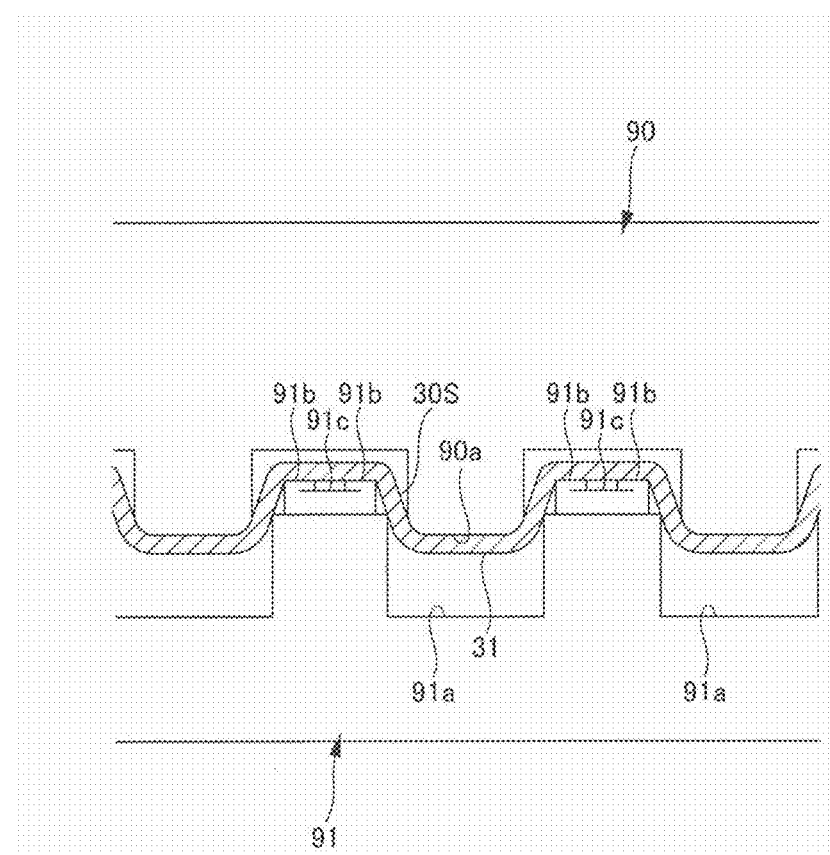
FIG. 17 is an enlarged cross-sectional view of essential portions of the squeeze roll and the recessed roll during formation of extruded protrusions.

For processing, the non-woven fabric 30S to be the top sheet 30 is transferred by being drawn from downstream of the production line, fed between the squeeze roll 90 and the recessed roll 91, as illustrated in FIG. 17, and is embossed by pushing the convexes of the squeeze roll 90 into the concaves 91$a$ of the recessed roll 91, into the extruded protrusions 31.

Figure 18:
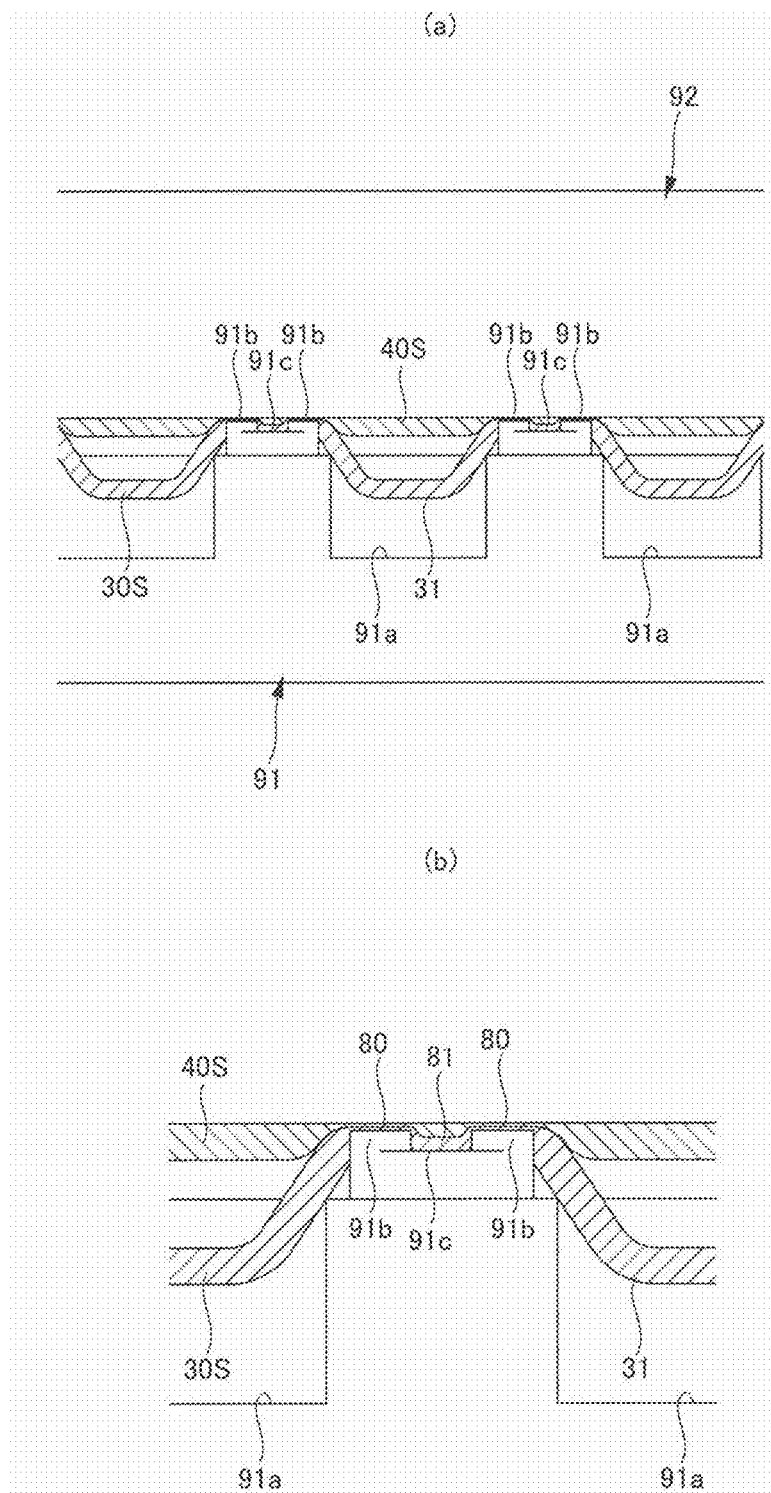
FIGS. 18(a) and 18(b) are enlarged cross-sectional views of essential portions of the recessed roll and the bonding roll during bonding.

Then, while the non-woven fabric 30S having the extruded protrusions 31 is wound around the recessed roll 91 so as to be guided directly, the material 40S of the second sheet is fed onto the outer side of the non-woven fabric to be the top sheet 30 by being drawn from downstream of the production line; and the non-woven fabric 30S to be the top sheet 30 and the material 40S of the second sheet are fed between the recessed roll 91 and the bonding roll 92, as illustrated in FIG. 18, compressed between the compression convexes 91$e$ of the recessed roll 91 and the circumferential surface of the bonding roll 92, and pressure welded between the bonding convexes 91$b$ of the recessed roll 91 and the circumferential surface of the bonding roll 92, into the top-second bonded portions 80 and thereby an assembly of the top sheet 30 and the second sheet 40. In this way, even if vertical wrinkles are formed between extruded protrusions 31 adjacent each other in the MD of the non-woven fabric 30S to be the top sheet 30 during the formation of the extruded protrusions 31, pressure-welded portions 80 and unwelded compressed portions 81 are formed during bonding of the non-woven fabric 30S to be the top sheet 30 and the material 40S of the second sheet such that they alternate in the CD and they are provided across the vertical wrinkles. Thus, the top-second bonded portions 80 can be formed while the vertical wrinkles are significantly stretch, and this stretched state can be maintained or substantially maintained even after production. The bonded areas intermittently aligned in CD provide adequate softness and satisfactory appearance. As understandable through this principle, not only compression by the compression convexes 91$e$ that leaves marks that serve as the compressed portions 81 but also compression that leave absolutely or substantially no marks are effective for prevention of vertical wrinkles. Either of these cases are included in the method for producing absorbent article according to the present invention.

Any pressure welder may be selected that compresses a material in the thickness direction and welds the material. Examples of such a pressure welder include a heat seal that heats a roll to weld the material and an ultrasonic seal. The assembly of the processed top sheet 30 and the second sheet 40 can be attached to the absorber through a known scheme, to produce a disposable diaper.

The bonding pattern according to the present invention is preferably applied to a processing scheme for bonding the top sheet 30 to the material of the second sheet 40 immediately after the extruded protrusions 31 are formed and before the wrinkles formed can be absorbed, as in the configuration illustrated in FIG. 12. If the top-second bonded portions 80 are to be formed after the extruded protrusions 31 are formed through embossing, the processing equipment may not always be the triple roll processing equipment described above. In the example illustrated in the drawing, the non-woven fabric to be the top sheet 30 is directly fed into the section where the squeeze roll 90 engages with the recessed roll 91. Alternatively, the non-woven fabric to be the top sheet 30 fed in the tangential direction of the circumferential surface of the squeeze roll 90 and wound only around the squeeze roll 90 may be fed directly between the squeeze roll 90 and the recessed roll 91 and guided onto the circumferential surface of the recessed roll 91.

Descriptions of Terms Used in Specification

The following terms should be understood to have the meanings defined below unless otherwise defined in this specification.
(Basis Weight)
The basis weight of a sheet composed of a material such as non-woven fabric is measured as follows. After preliminary drying of a sample or test piece, the sample or test piece is left in a test room or a test device under normal conditions (an ambient temperature of 20±5° C. and a relative humidity of 65% or less) until the weight of the sample or test piece reaches constant mass. Preliminary drying is to achieve the constant mass of the sample or test piece under an environment having a relative humidity within the range of 10% to 25% and a temperature not exceeding 50° C. For fibers having a standard moisture regain of 0.0%, preliminary drying may be omitted. The test piece having constant mass is cut with a cutting template (200×250 mm, ±2 mm) into samples of 200×250 mm (±2 mm). The weight of the sample is measured. The measured weight is multiplied by 20 to determine the weight per square meter, which is defined as the basis weight.
(Thickness)
Thickness is automatically measured with an automatic thickness gauge (KES-G5 handy compression measurement program) under a load of 10 gf/cm$^2$ in a pressurized area of 2 cm$^2$.
(Direction)
"Front-back direction (longitudinal direction)" is the direction connecting the ventral side (front side) and the dorsal side (back side). "Width direction" is the direction orthogonal to the front-back direction (right-left direction). "Up-down direction" is the direction orthogonal to the width direction of the diaper after wearing the diaper, i.e., folded at the crotch portion to overlay the ventral side portion and the dorsal side portion of the diaper.
(Extension Ratio)
"Extension ratio" refers to a value with respect to 100% representing the natural length.
(Water Absorption Capacity)
Water absorption capacity is measured in accordance with JIS K7223-1996 standard "Testing Method for Water Absorption Capacity of Superabsorbent Polymers."
(Water Absorption Rate)
Water absorption rate is defined as "time that elapses before the end point" measured with superabsorbent polymers (2 g) and a normal saline solution (50 g) in accordance with JIS K7224-1996 "Testing Method for Water Absorption Rate of Super Absorbent Polymers."

REFERENCE SIGNS LIST

11 liquid impervious sheet, 12 outer sheet, 12T target sheet, 13 fastening tape, 13A engage portion, 13B tape main unit section, 13C tape attachment section, 30 top sheet, 31 extruded protrusion, 40 second sheet, 50 absorbent element, 56 absorber, 58 package sheet, 60 three-dimensional side gather, 62 gather sheet, 70 dorsal side stretchable waist sheet, 80 top-second bonded portion, 90 squeeze roll, 90a squeeze convex, 91 recessed roll, 91a concave, 91b bonding convex, 92 bonding roll, 81 compressed portion, 91e compression convex

The invention claimed is:
1. A method of producing an absorbent article comprising an absorber, a liquid pervious top sheet comprising a non-woven fabric covering a front side of the absorber, and a second sheet bonded to a back side of the top sheet, wherein a plurality of of extruded protrusions embossed from the back side to a front side of the top sheet is arrayed at intervals in a width direction and a front-back direction respectively, and a plurality of top-second bonded portions arrayed in an intermittent bonding pattern in the width direction and the front-back direction is provided through pressure welding of the top sheet and the second sheet at areas between the extruded protrusions adjacent each other in the width direction and the front-back direction, the method comprising:
 assembling the top sheet and the second sheet, the assembling comprising:
  transferring the non-woven fabric to be the top sheet by being drawn from downstream of a production line while forming the extruded protrusions in the non-woven fabric through embossing;
  after said transferring the non-woven fabric, aligning a material of the second sheet with a back side of the non-woven fabric having the extruded protrusions; and
  bonding the non-woven fabric and the material of the second sheet into a bonding pattern such that in regions between the extruded protrusions adjacent each other in a machine direction, rows of a plurality of top-second bonded portions disposed at intervals in a cross direction orthogonal to the machine direction are provided through center positions of the regions in the cross direction,
 wherein areas between the top-second bonded portions in the cross section comprise compressed portions in each of which the top sheet and the second sheet are unwelded and the top sheet is more highly compressed than areas at both sides of the compressed portions in the machine direction, the compressed portions being concave and being formed on the front side of the top sheet, and a back surface of the compressed portion contacting the second sheet and being devoid of a space between the back surface of the compressed portion and the second sheet.
2. The method of producing an absorbent article according to claim 1, wherein in the bonding pattern, the top-second bonded portions are absent, the non-woven fabric and the material of the second sheet are unwelded, and the non-woven fabric is compressed in the center positions in the cross direction corresponding to center portions in the cross direction CD of the extruded protrusions adjacent each other in the machine direction.

3. The method of producing an absorbent article according to claim 1, wherein, in the bonding pattern:
   a plurality of rows of the top-second bonded portions is formed at intervals in the machine direction in the regions, each row comprising the plurality of top-second bonded portions aligned in the cross direction at intervals;
   the non-woven fabric and the material of the second sheet are unwelded and the non-woven fabric is compressed in areas between the top-second bonded portions in the cross direction; and
   the non-woven fabric and the material of the second sheet are unwelded and the non-woven fabric is more lightly compressed in areas between the top-second bonded portions in the machine direction compared to the areas in the cross direction.

4. The method of producing an absorbent article according to claim 1, wherein a squeeze roll having a large number of squeeze convexes is disposed in a pattern corresponding to the pattern of the extruded protrusions on the circumferential surface of the squeeze roll, a recessed roll faces the squeeze roll, having concaves corresponding to the squeeze convexes, and having bonding convexes that form the top-second bonded portions and compression convexes provided between the concaves, and a bonding roll faces the recessed roll, and
   wherein the non-woven fabric to be the top sheet is transferred by being drawn from downstream of the production line and is fed between the squeeze roll and the recessed roll, the squeeze convexes of the squeeze roll are pushed into the bonding concaves of the recessed roll to form the extruded protrusions and then, while the non-woven fabric to be the top sheet is wound around the rotating recessed roll so as to be guided directly, the material of the second sheet is being fed onto the outer side of the non-woven fabric to be the top sheet by being drawn from the downstream of the production line, the non-woven fabric to be the top sheet and the material of the second sheet are being fed between the recessed roll and the bonding roll, the non-woven fabric to be the top sheet and the material of the second sheet are pressure welded between the bonding convexes of the recessed roll and the outer circumferential surface of the bonding roll, to form the top-second bonded portions.

5. An absorbent article comprising:
   an absorber;
   a liquid pervious top sheet comprising a non-woven fabric covering a front side of the absorber;
   a second sheet bonded to a back side of the top sheet;
   a plurality of extruded protrusions embossed from the back side to a front side of the top sheet and arrayed in a width direction and a front-back direction at intervals;
   a plurality of dot-shaped top-second bonded portions disposed in an intermittent bonding pattern in the width direction and the front-back direction of the top sheet, the plurality of dot-shaped top-second bonded portions being provided through pressure welding of the top sheet at areas between the extruded protrusions adjacent each other in the width direction and the front-back direction and the second sheet; and
   rows of a plurality of top-second bonded portions disposed in the top sheet at intervals in a cross direction in regions between the extruded protrusions adjacent each other in a machine direction, the machine direction being orthogonal to the cross direction, provided across center positions of the regions in the cross direction,
   wherein areas between the top-second bonded portions in the cross section comprise compressed portions in each of which the top sheet and the second sheet are unwelded and the top sheet is more highly compressed than areas at both sides of the compressed portions in the machine direction, the compressed portions being concave and being formed on the front side of the top sheet, and a back surface of the compressed portion contacting the second sheet and being devoid of a space between the back surface of the compressed portion and the second sheet.

6. The absorbent article according to claim 5, wherein the compressed portions are disposed and the top-second bonded portions are absent at center positions in the cross direction corresponding to center portions in the cross direction of the extruded protrusions adjacent each other in the machine direction.

7. The absorbent article according to claim 5, further comprising:
   a plurality of rows of top-second bonded portions formed at intervals in the machine direction in the regions, the plurality of top-second bonded portions being aligned in the cross direction at intervals,
   wherein the top sheet and the second sheet are unwelded and the top sheet is compressed in areas between the top-second bonded portions in the cross direction, and
   wherein the top sheet and the second sheet are unwelded and the top sheet is more lightly compressed in areas between the top-second bonded portions in the machine direction compared to areas between top-second bonded portions in the cross direction.

8. The absorbent article according to claim 5, wherein the top-second bonded portions in the regions comprise dot-shaped bonded portions having a machine direction length 0.1 to 0.4 times a machine direction center pitch of cross direction rows of the extruded protrusions adjacent each other in the machine direction and a cross direction length 0.1 to 0.4 times a cross direction center pitch of machine direction rows of extruded protrusions adjacent each other in the cross direction, and
   wherein a distance between adjacent top-second bonded portions in the cross direction among rows of the plurality of top-second bonded portions disposed at intervals in the cross direction is 1 to 5 times a cross direction length of the top-second bonded portions.

9. The absorbent article according to claim 5, wherein the machine direction is a front-back direction of the absorbent article, and the cross direction is a width direction of the absorbent article, or
   wherein the machine direction is the width direction of the absorbent article, and the cross direction is the front-back direction of the absorbent article.

10. The method of producing an absorbent article according to claim 2, wherein a squeeze roll having a large number of squeeze convexes is disposed in a pattern corresponding to the pattern of the extruded protrusions on the circumferential surface of the squeeze roll, a recessed roll faces the squeeze roll, having concaves corresponding to the squeeze convexes, and having bonding convexes that form the top-second bonded portions and compression convexes provided between the concaves, and a bonding roll faces the recessed roll, and
   wherein the non-woven fabric to be the top sheet is transferred by being drawn from downstream of the production line and is fed between the squeeze roll and the recessed roll, the squeeze convexes of the squeeze roll are pushed into the bonding concaves of the recessed roll to form the extruded protrusions and then, while the non-woven fabric to be the top sheet is wound around the rotating recessed roll so as to be guided directly, the material of the second sheet is being fed onto the outer side of the non-woven fabric to be the top sheet by being drawn from the downstream of the production line, the non-woven fabric to be the top sheet and the material of the second sheet are being fed between the recessed roll and the bonding roll, the non-woven fabric to be the top sheet and the material of the second sheet are pressure welded between the bonding convexes of the recessed roll and the outer circumferential surface of the bonding roll, to form the top-second bonded portions.

11. The method of producing an absorbent article according to claim 3, wherein a squeeze roll having a large number of squeeze convexes is disposed in a pattern corresponding to the pattern of the extruded protrusions on the circumferential surface of the squeeze roll, a recessed roll faces the squeeze roll, having concaves corresponding to the squeeze convexes, and having bonding convexes that form the top-second bonded portions and compression convexes provided between the concaves, and a bonding roll faces the recessed roll, and wherein the non-woven fabric to be the top sheet is transferred by being drawn from downstream of the production line and is fed between the squeeze roll and the recessed roll, the squeeze convexes of the squeeze roll are pushed into the bonding concaves of the recessed roll to form the extruded protrusions and then, while the non-woven fabric to be the top sheet is wound around the rotating recessed roll so as to be guided directly, the material of the second sheet is being fed onto the outer side of the non-woven fabric to be the top sheet by being drawn from the downstream of the production line, the non-woven fabric to be the top sheet and the material of the second sheet are being fed between the recessed roll and the bonding roll, the non-woven fabric to be the top sheet and the material of the second sheet are pressure welded between the bonding convexes of the recessed roll and the outer circumferential surface of the bonding roll, to form the top-second bonded portions.

12. The absorbent article according to claim 6, further comprising a plurality of rows of the top-second bonded portions formed at intervals in the machine direction in the regions, the plurality of top-second bonded portions being aligned in the cross direction at intervals, wherein the top sheet and the second sheet are unwelded and the top sheet is compressed in areas between the top-second bonded portions in the cross direction, and wherein the top sheet and the second sheet are unwelded and the top sheet is more lightly compressed in areas between the top-second bonded portions in the machine direction compared to the areas between top-second bonded portions in the cross direction.

13. The absorbent article according to claim 6, wherein the top-second bonded portions in the regions comprise dot-shaped bonded portions having a machine direction length 0.1 to 0.4 times a machine direction center pitch of cross direction rows of the extruded protrusions adjacent each other in the machine direction and a cross direction length 0.1 to 0.4 times a cross direction center pitch of machine direction rows of extruded protrusions adjacent each other in the cross direction, and wherein a distance between adjacent top-second bonded portions in the cross direction among rows of the plurality of top-second bonded portions disposed at intervals in the cross direction is 1 to 5 times a cross direction length of the top-second bonded portions.

14. The absorbent article according to claim 7, wherein the top-second bonded portions in the regions comprise dot-shaped bonded portions having a machine direction length 0.1 to 0.4 times a machine direction center pitch of cross direction rows of the extruded protrusions adjacent each other in the machine direction and a cross direction length 0.1 to 0.4 times a cross direction center pitch of machine direction rows of extruded protrusions adjacent each other in the cross direction, and wherein a distance between adjacent top-second bonded portions in the cross direction among rows of the plurality of top-second bonded portions disposed at intervals in the cross direction is 1 to 5 times a cross direction length of the top-second bonded portions.

15. The absorbent article according to claim 6, wherein the machine direction is a front-back direction of the absorbent article, and the cross direction is a width direction of the absorbent article, or wherein the machine direction is the width direction of the absorbent article, and the cross direction is the front-back direction of the absorbent article.

16. The absorbent article according to claim 7, wherein the machine direction is a front-back direction of the absorbent article, and the cross direction is a width direction of the absorbent article, or wherein the machine direction is the width direction of the absorbent article, and the cross direction is the front-back direction of the absorbent article.

17. The absorbent article according to claim 8, wherein the machine direction is a front-back direction of the absorbent article, and the cross direction is a width direction of the absorbent article, or wherein the machine direction is the width direction of the absorbent article, and the cross direction is the front-back direction of the absorbent article.

* * * * *